US010767229B2

(12) United States Patent
Lindley

(10) Patent No.: US 10,767,229 B2
(45) Date of Patent: Sep. 8, 2020

(54) METHODS FOR DETERMINING THE CAUSE OF SOMATIC MUTAGENESIS

(71) Applicant: GMDx Co Pty Ltd, Melbourne, Victoria (AU)

(72) Inventor: Robyn Alice Lindley, Melbourne (AU)

(73) Assignee: GMDX CO PTY LTD, Melbourne, Victoria (AU)

(*) Notice: Subject to any disclaimer, the term of this patent is extended or adjusted under 35 U.S.C. 154(b) by 292 days.

(21) Appl. No.: 14/440,837

(22) PCT Filed: Nov. 5, 2013

(86) PCT No.: PCT/AU2013/001275
§ 371 (c)(1),
(2) Date: May 5, 2015

(87) PCT Pub. No.: WO2014/066955
PCT Pub. Date: May 8, 2014

(65) Prior Publication Data
US 2015/0284803 A1    Oct. 8, 2015

(30) Foreign Application Priority Data

Nov. 5, 2012   (AU) ................. 2012904826
Nov. 13, 2012  (AU) ................. 2012904940
Apr. 12, 2013  (AU) ................. 2013901253

(51) Int. Cl.
*C12Q 1/6886* (2018.01)
*A61N 5/10* (2006.01)
(52) U.S. Cl.
CPC ............. *C12Q 1/6886* (2013.01); *A61N 5/10* (2013.01); *C12Q 2600/142* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

2013/0210900 A1* 8/2013 Vogelstein ......... A61K 31/7088
514/44 R

OTHER PUBLICATIONS

Martincorena (Science vol. 349 Issue 6255 Sep. 25, 2015 pp. 1483-1489).*
Burns (Nature Genetics vol. 45 No. 9 Sep. 2013 pp. 977-984).*
Griffiths (An Introduction to Genetic Analysis. 7th edition. New York: W. H. Freeman; 2000. Somatic versus germinal mutation. Available from: https://www.ncbi.nlm.nih.gov/books/NBK21894/).*
Conticello (Genome Biology 2008 vol. 9 pp. 229.1-229.10).*
Gene Card for APOBEC3G (found online at https://www.genecards.org/cgi-bin/carddisp.pl?gene=APOBEC3G accessed online Dec. 20, 2018).*
Conticello, Silvestro G. "The AID/APOBEC family of nucleic acid mutators," Genome Biology, 2008;9:229.1-229.10.
Yang, Ziheng et al., "Likelihood Models of Somatic Mutation and Codon Substitution in Cancer Genes," Genetics 165: 695-705, Oct. 2003.
Beale, R.C.L., et al, Comparison of the Differential Context-dependence of DNA Deamination by APOBEC Enzymes: Correlation with Mutation Spectra In Vivo, J. Mol. Biol., vol. 337, pp. 585-596, 2004.
Du, L., et al., A Regulatory Role for NBS1 in Strand-Specific Mutagenesis during Somatic Hypermutation, PLoS ONE, vol. 3, No. 6, e2482, 2008.
Grant, H., et al., Analysis of BCR-ABL1 Tyrosine Kinase Domain Mutational Spectra in Primitive Chronic Myeloid Leukemia Cells Suggests a Unique Mutator Phenotype, Leukemia, vol. 24, pp. 1817-1821, 2010.
Li, M., et al, First-In-Class Small Molecule Inhibitors of the Single-Strand DNA Cytosine Deaminase APOBEC3G, ACS Chem. Biol., vol. 7, pp. 506-517, 2012.
Olivier, M., et al, TP53 Mutations in Human Cancers: Origins, Consequences, and Clinical Use, Cold Spring Harb Perspect Biol, 2010;2:a001008.
Roberts, S.A., et al, Clustered Mutations in Yeast and in Human Cancers Can Arise from Damaged Long Single-Strand DNA Regions, Molecular Cell, vol. 46, pp. 424-435, May 25, 2012.
Jiang, X. et al. "Analysis of BCR-ABL1 Tyrosine Kinase Domain Mutations in Primitive Chronic Myeloid Leukemia Cells Identifies a Unique Mutator Phenotype", Blood, 2010, vol. 116, No. 21, pp. 1390-1391.
Shapiro, G.S. et al. "DNA Target Motifs of Somatic Mutagenesis in Antibody Genes", Critical Reviews in Immunology, 2002, vol. 22, pp. 183-200.
Beale, R.C.L. et al. "Comparison of the Differential Context-dependent of DNA Deamination by APOBEC Enzymes: Correlation with Mutation Spectra in Vivo", Journal of Molecular Biology, 2004, vol. 337, pp. 585-596.
Cerruti, P. et al. "Mutagenesis of the H-ras Protooncogene and the p53 Tumor Suppressor Gene", Cancer Research, 1994, vol. 54. pp. 1934s-1938s.
Cherpillod, P. et al. "Benzo[a]pyrene-Induced Mutagenesis of p53 Hot-Spot Codons 248 and 249 in Human Hepatocyes", Molecular Carcinogenesis, 1995, vol. 13, pp. 15-20.

(Continued)

*Primary Examiner* — Amanda Haney
(74) *Attorney, Agent, or Firm* — Knobbe, Martens, Olson & Bear, LLP

(57) ABSTRACT

The invention relates generally to methods for determining the likelihood that targeted somatic mutagenesis of a nucleic acid molecule by a mutagenic agent has occurred, and the likelihood that a mutagenic agent is a cause of targeted somatic mutagenesis of a nucleic acid molecule. The invention further relates to methods for diagnosing cancer in a subject and/or determining the likelihood that a subject has or will develop cancer, and methods for treating subjects diagnosed with cancer or determined to be likely to have or to develop cancer. In further aspects, the invention relates to methods for identifying motifs in nucleic acid molecules that are recognized or targeted by mutagenic agents.

5 Claims, 19 Drawing Sheets

(56) References Cited

OTHER PUBLICATIONS

Oda, H. et al. "A mutational hot spot in the p53 gene is associated with hepatoblastomas", International Journal of Cancer, 1995, vol. 60, pp. 786-790.
Baysal, B.E. "A Recurrent Stop-Codon Mutation in Succinate Dehydrogenase Subunit B Gene in Normal Peripheral Blood and Childhood T-Cell Acute Leukemia", PloS One, 1995, vol. 2, e436.
Nik-Zainal, S. et al. "Mutational Processes Modelling the Genomes of 21 Breast Cancers", Cell, 2012, vol. 149, pp. 979-993 (May 25, 2012).
Petit, V., et al., "Powerful mutators lurking in the genome", Philosophical Transactions of the Royal Society B., 2009, vol. 364, pp. 705-715.
Roberts, S.A. et al. "Clustered Mutations in Yeast and in Human Cancers Can Arise from Damaged Long Single-Strand DNA Regions", Molecular Cell, 2012, vol. 46, pp. 424-435 (May 25, 2012).
Lindley, R.A. "The importance of codon context for understanding the Ig-like somatic hypermutation strand-biased patterns in TP53 mutations in breast cancer", Cancer Genetics, 2013, vol. 206, pp. 222-226.
International Search Report dated Jan. 29, 2014 for PCT/AU2013/001275.
Beale, R.C.L., et al., Comparison of the Differential Context-Dependence of DNA Deamination by APOBEC Enzymes: Correlation with Mutation Spectra in Vivo, Journal of Molecular Biology, vol. 337, pp. 585-596, 2004.
Bishop, K.N., et al., Cytidine Deamination of Retroviral DAN by Diverse APOBEC Proteins, Current Biology, vol. 14, pp. 1392-1396, 2004.
Dang, Y., et al., Identification of APOBEC3DE as Another Antiretroviral Factor from the Human APOBEC Family, Journal of Virology, vol. 80, No. 21, pp. 10522-10533, 2016.
Henry, M., et al., Genetic Editing of HBV DNA by Monodomain Human APOBEC3 Cytidine Deaminases and the Recombinant Nature of APOBEC3G, PLoS One, vol. 4, No. 1, e4277, 2009.
Kohli, R.M., et al., Local Sequence Targeting in the AID/APOBEC Family Differentially Impacts Retroviral Restriction and Antibody Diversification, The Journal of Biological Chemistry, vol. 285, No. 52, pp. 40956-40964, 2010.
Rathore, A., et al., The Local Dinucleotide Preference of ABOBEC3G Can be Altered from 5'-CC to 5'-TC by a Single Amino Acid Substitution, Journal of Molecular Biology, vol. 425, No. 22, pp. 1-21, 2013.
Shinohara, M., et al., APOBEC3B Can Impair Genomic Stability by Inducing Base Substitutions in Genomic DNA in Human Cells, Scientific Reports, vol. 2 : 806, pp. 1-9, 2014.
Thielen, B.K., et al., Innate Immune Signaling Induces High Levels of TC-Specific Deaminase Activity in Primary Monocyte-Derived Cells Through Expression of APOBEC3A Isoforms, The Journal of Biological Chemistry, vol. 285, No. 36, pp. 27753-27766, 2010.
Yu, Q., et al., APOBEC3B and APOBEC3C Are Potent Inhibitors of Simian Immunodeficiency Virus Replication, The Journal of Biological Chemistry, vol. 279, No. 51, pp. 53379-53386, 2004.

\* cited by examiner

Figure 2

Identification of targeted somatic mutation in a nucleic acid molecule

1. Analyse sequence of non-transcribed strand of nucleic acid for single point mutations and note the type of mutation, codon context of the mutation and nucleotides flanking the mutation, and identify those at APOBEC3G and AID motifs.

| Sample | cDNA | 5' Codon | Mutated Codon | 3' Codon/IC1- | WT | Mut | WA | APO3G CG | CG | AID WRC | GYW |
|---|---|---|---|---|---|---|---|---|---|---|---|
| PD3185a | c.1474C>T | CTA | CGG | GGA | 1 | C | T | | | | WRC | |
| PD3185a | c.289C>T | CAA | CGC | TCC | 1 | C | T | | | | WRC | |
| PD3185a | c.31G>T | AAG | GCA | CCT | 1 | G | T | | | | | GYW |
| PD3185a | c.2248G>T | CTG | GGC | TGG | 1 | G | T | | | | | |
| PD3185a | c.3869C>G | GAA | ACT | GAA | 2 | C | G | | | | WRC | |
| PD3185a | c.527G>A | TTT | CGC | AAT | 2 | G | A | | |  | | GYW |
| PD3185a | c.4256G>A | ATT | CGT | GGC | 2 | G | A | | | CG | | |
| PD3185a | c.8G>A | TTG | CGG | TTG | 2 | G | A | | | CG | | |
| PD3185a | c.495C>T | GTA | AAC | TCG | 3 | C | T | | | | WRC | |
| PD3185a | c.495C>T | GTA | AAC | TCG | 3 | C | T | | | | WRC | |
| PD3185a | c.1473C>T | AGG | GGC | TAC | 3 | C | T | | | | | |

↓

2. Tabulate the mutation spectra and calculate the likelihood that the mutations arose by chance. To avoid double-counting of the mutations that are co-incident with 2 known motifs, duplicates (highlighted above) are removed according to a desired hierarchy, e.g. AID over APOBEC3G.

TSM Test for AID/APO activity

| Mutation Type | Location of mutations | | | |
|---|---|---|---|---|
| | MC-1 | MC-2 | MC-3 | Total |
| GYW/WRC sites (AID) | | | | |
| G>A | 0 | 1 | 0 | 1 |
| G>T | 1 | 0 | 0 | 1 |
| G>C | 0 | 0 | 0 | 0 |
| C>A | 0 | 0 | 0 | 0 |
| C>T | 2 | 0 | 2 | 4 |
| C>G | 0 | 1 | 0 | 1 |
| CG/CG sites (APOBEC3G) | | | | |
| G>A | 0 | 2 | 0 | 2 |
| G>T | 0 | 0 | 0 | 0 |
| G>C | 0 | 0 | 0 | 0 |
| C>A | 0 | 0 | 0 | 0 |
| C>T | 0 | 0 | 0 | 0 |
| C>G | 0 | 0 | 0 | 0 |
| WA sites | | | | |
| A>T | 0 | 0 | 0 | 0 |
| A>C | 0 | 0 | 0 | 0 |
| A>G | 0 | 0 | 0 | 0 |

Sample: PD3185a
Mutations ($n$): 11
TSM Activation: AID/APO3G POSITIVE
Significance ($p$ value): 0.00083897

| Diagnostic Categories | Observed | Expected |
|---|---|---|
| 1. G>A mutations off the GYW motif at MC-2 sites | 1.00 | 0.333 |
| 2. C>T mutations off the WRC motif at MC-1 sites | 2.00 | 0.500 |
| 3. G>A mutations off the CG motif at MC-2 sites | 2.00 | 0.333 |
| 4. C>T mutations off the CG motif at MC-1 sites | 0.00 | 0.000 |
| 5. A>G mutations off WA motif at MC-2 sites | 0.00 | 0.000 |

Comments:

Figure 3

Haematopoietic & Lymphoid Tissue - TET2
(n = 615)

| Mutation Type | Location of mutations | | | |
|---|---|---|---|---|
| | MC-1 | MC-2 | MC-3 | Total |
| GYW/WRC sites (AID) | | | | |
| G>A | 4 | 11 | 2 | 17 |
| G>T | 10 | 3 | 0 | 13 |
| G>C | 0 | 1 | 1 | 2 |
| C>A | 1 | 1 | 5 | 7 |
| C>T | 72 | 6 | 0 | 78 |
| C>G | 1 | 1 | 7 | 9 |
| CG/CG sites (APOBEC3G) | | | | |
| G>A | 2 | 7 | 1 | 10 |
| G>T | 7 | 0 | 0 | 7 |
| G>C | 0 | 1 | 0 | 1 |
| C>A | 1 | 0 | 0 | 1 |
| C>T | 84 | 1 | 3 | 88 |
| C>G | 0 | 1 | 3 | 4 |
| WA sites | | | | |
| A>T | 4 | 0 | 0 | 4 |
| A>C | 1 | 2 | 0 | 3 |
| A>G | 13 | 2 | 1 | 16 |

C>T mutations off the WRC motif at MC-1 sites

Observed (O) = 72

Expected (E) = (72+10)/6 = 13.67

| Diagnostic Categories | Observed | Expected |
|---|---|---|
| 1. G>A mutations off the GYW motif at MC-2 sites | 11 | 4.83 |
| 2. C>T mutations off the WRC motif at MC-1 sites | 72 | 13.67 |
| 3. G>A mutations off the CG motif at MC-2 sites | 7 | 2.83 |
| 4. C>T mutations off the CG motif at MC-1 sites | 84 | 14.50 |
| 5. A>G mutations off WA motif at MC-2 sites | 2 | 3.67 |

CHI, SUARE7.42E-128

Figure 4

| Cervix - "All Cervix" | | | | |
|---|---|---|---|---|
| Mutation Type | Location of mutations | | | |
| | MC-1 | MC-2 | MC-3 | Total |
| GYW/WRC sites (AID) | | | | |
| G>A | 0 | 1 | 1 | 2 |
| G>T | 0 | 3 | 0 | 3 |
| G>C | 0 | 1 | 0 | 1 |
| C>A | 0 | 0 | 0 | 0 |
| C>T | 9 | 0 | 1 | 10 |
| C>G | 0 | 0 | 1 | 1 |
| CG/CG sites (APOBEC3G) | | | | |
| G>A | 3 | 16 | 0 | 19 |
| G>T | 0 | 1 | 0 | 1 |
| G>C | 0 | 2 | 0 | 2 |
| C>A | 1 | 0 | 0 | 1 |
| C>T | 12 | 0 | 0 | 12 |
| C>G | 0 | 0 | 0 | 0 |
| TG/CA (APOBEC1) | | | | |
| G>A | 3 | 2 | 3 | 8 |
| G>T | 1 | 1 | 0 | 2 |
| G>C | 0 | 0 | 0 | 0 |
| C>A | 0 | 0 | 0 | 0 |
| C>T | 2 | 0 | 3 | 5 |
| C>G | 0 | 0 | 0 | 0 |
| WA sites | | | | |
| A>T | 0 | 0 | 0 | 0 |
| A>C | 0 | 0 | 0 | 0 |
| A>G | 0 | 3 | 0 | 3 |

| Diagnostic Categories | Observed | Expected |
|---|---|---|
| 1. G>A mutations off the GYW motif at MC-2 sites | 1 | 0.83 |
| 2. C>T mutations off the WRC motif at MC-1 sites | 9 | 1.50 |
| 3. G>A mutations off the CG motif at MC-2 sites | 16 | 3.67 |
| 4. C>T mutations off the CG motif at MC-1 sites | 12 | 2.17 |
| 5. A>G mutations off WA motif at MC-2 sites | 3 | 0.50 |
| | CHI, SUARE | 1.88581E-28 |

Figure 5

| Colon - Adenocarcinoma | | | | |
|---|---|---|---|---|
| Mutation | Location of mutation | | | |
| Type | MC-1 | MC-2 | MC-3 | Total |
| GYW/WRC sites (AID) | | | | |
| G>A | 0 | 9 | 3 | 12 |
| G>T | 1 | 5 | 1 | 7 |
| G>C | 1 | 0 | 0 | 1 |
| C>A | 0 | 0 | 5 | 5 |
| C>T | 36 | 0 | 0 | 36 |
| C>G | 0 | 0 | 0 | 0 |
| CG/CG sites (APOBEC3G) | | | | |
| G>A | 19 | 106 | 0 | 125 |
| G>T | 2 | 4 | 0 | 6 |
| G>C | 0 | 3 | 0 | 3 |
| C>A | 0 | 0 | 0 | 0 |
| C>T | 95 | 2 | 0 | 97 |
| C>G | 2 | 0 | 0 | 2 |
| TG/CA (APOBEC1) | | | | |
| G>A | 2 | 10 | 3 | 15 |
| G>T | 2 | 5 | 0 | 7 |
| G>C | 1 | 0 | 0 | 1 |
| C>A | 0 | 0 | 0 | 0 |
| C>T | 5 | 0 | 1 | 6 |
| C>G | 0 | 0 | 0 | 0 |
| WA sites | | | | |
| A>T | 0 | 0 | 0 | 0 |
| A>C | 0 | 3 | 0 | 3 |
| A>G | 1 | 11 | 0 | 12 |

| Diagnostic Categories | Observed | Expected |
|---|---|---|
| 1. G>A mutations off the GYW motif at MC-2 sites | 9 | 2.67 |
| 2. C>T mutations off the WRC motif at MC-1 sites | 36 | 6.00 |
| 3. G>A mutations off the CG motif at MC-2 sites | 106 | 22.33 |
| 4. C>T mutations off the CG motif at MC-1 sites | 95 | 16.50 |
| 5. A>G mutations off WA motif at MC-2 sites | 11 | 2.50 |
| CHI, SUARE | 2.349E-189 | |

Figure 6

| Liver - Hepatocellular Carcinoma (HCC) | | | | |
|---|---|---|---|---|
| Mutation Type | Location of mutations | | | |
| | MC-1 | MC-2 | MC-3 | Total |
| GYW/WRC sites (AID) | | | | |
| G>A | 1 | 13 | 3 | 17 |
| G>T | 2 | 11 | 2 | 15 |
| G>C | 0 | 7 | 0 | 7 |
| C>A | 3 | 0 | 5 | 8 |
| C>T | 28 | 0 | 1 | 29 |
| C>G | 0 | 0 | 7 | 7 |
| CG/CG sites (APOBEC3G) | | | | |
| G>A | 5 | 31 | 0 | 36 |
| G>T | 28 | 23 | 1 | 52 |
| G>C | 9 | 8 | 0 | 17 |
| C>A | 5 | 2 | 2 | 9 |
| C>T | 49 | 1 | 0 | 50 |
| C>G | 1 | 0 | 0 | 1 |
| TG/CA (APOBEC1) | | | | |
| G>A | 4 | 19 | 4 | 27 |
| G>T | 6 | 11 | 2 | 19 |
| G>C | 1 | 3 | 1 | 5 |
| C>A | 0 | 0 | 0 | 0 |
| C>T | 11 | 0 | 1 | 12 |
| C>G | 0 | 0 | 0 | 0 |
| WA sites | | | | |
| A>T | 4 | 3 | 1 | 8 |
| A>C | 0 | 4 | 0 | 4 |
| A>G | 4 | 36 | 1 | 41 |
| GG sites | | | | |
| G>A | 16 | 9 | 2 | 27 |
| G>T | 14 | 9 | 184 | 207 |
| G>C | 4 | 6 | 7 | 17 |

| Diagnostic Categories | Observed | Expected |
|---|---|---|
| 1. G>A mutations off the GYW motif at MC-2 sites | 13 | 5.67 |
| 2. C>T mutations off the WRC motif at MC-1 sites | 28 | 5.17 |
| 3. G>A mutations off the CG motif at MC-2 sites | 31 | 17.33 |
| 4. C>T mutations off the CG motif at MC-1 sites | 49 | 9.67 |
| 5. A>G mutations off WA motif at MC-2 sites | 36 | 8.50 |

CHI, SUARE   7.6521E-79

Figure 7

| Pancreas – 'All Pancreas' | | | | |
|---|---|---|---|---|
| Mutation | Location of mutations | | | |
| Type | MC-1 | MC-2 | MC-3 | Total |
| GYW/WRC sites (AID) | | | | |
| G>A | 0 | 15 | 2 | 17 |
| G>T | 0 | 5 | 2 | 7 |
| G>C | 0 | 0 | 0 | 0 |
| C>A | 2 | 0 | 2 | 4 |
| C>T | 31 | 1 | 1 | 33 |
| C>G | 2 | 0 | 2 | 4 |
| CG/CG sites (APOBEC3G) | | | | |
| G>A | 6 | 63 | 0 | 69 |
| G>T | 3 | 5 | 0 | 8 |
| G>C | 0 | 5 | 0 | 5 |
| C>A | 1 | 1 | 0 | 2 |
| C>T | 59 | 0 | 0 | 59 |
| C>G | 5 | 0 | 0 | 5 |
| TG/CA (APOBEC1) | | | | |
| G>A | 8 | 12 | 4 | 24 |
| G>T | 4 | 3 | 2 | 9 |
| G>C | 2 | 0 | 0 | 2 |
| C>A | 0 | 0 | 0 | 0 |
| C>T | 6 | 0 | 0 | 6 |
| C>G | 0 | 0 | 0 | 0 |
| WA sites | | | | |
| A>T | 1 | 1 | 0 | 2 |
| A>C | 1 | 0 | 0 | 1 |
| A>G | 0 | 16 | 1 | 17 |

| Diagnostic Categories | Observed | Expected |
|---|---|---|
| 1. G>A mutations off the GYW motif at MC-2 sites | 15 | 3.33 |
| 2. C>T mutations off the WRC motif at MC-1 sites | 31 | 6.00 |
| 3. G>A mutations off the CG motif at MC-2 sites | 63 | 13.67 |
| 4. C>T mutations off the CG motif at MC-1 sites | 59 | 11.00 |
| 5. A>G mutations off WA motif at MC-2 sites | 16 | 3.17 |
| | CHI, SUARE | 3.4278E-125 |

Figure 8

| Prostate – 'All Prostate' | | | | |
|---|---|---|---|---|
| Mutation | Location of mutations | | | |
| Type | MC-1 | MC-2 | MC-3 | Total |
| GYW/WRC sites (AID) | | | | |
| G>A | 0 | 8 | 5 | 13 |
| G>T | 2 | 3 | 1 | 6 |
| G>C | 0 | 2 | 0 | 2 |
| C>A | 0 | 1 | 4 | 5 |
| C>T | 22 | 1 | 0 | 23 |
| C>G | 0 | 0 | 2 | 2 |
| CG/CG sites (APOBEC3G) | | | | |
| G>A | 5 | 34 | 3 | 42 |
| G>T | 0 | 3 | 0 | 3 |
| G>C | 0 | 2 | 0 | 2 |
| C>A | 1 | 0 | 0 | 1 |
| C>T | 30 | 2 | 0 | 32 |
| C>G | 3 | 0 | 1 | 4 |
| TG/CA (APOBEC1) | | | | |
| G>A | 2 | 5 | 10 | 17 |
| G>T | 4 | 5 | 1 | 10 |
| G>C | 0 | 0 | 0 | 0 |
| C>A | 0 | 0 | 0 | 0 |
| C>T | 3 | 2 | 0 | 5 |
| C>G | 0 | 0 | 0 | 0 |
| WA sites | | | | |
| A>T | 2 | 1 | 1 | 4 |
| A>C | 1 | 2 | 0 | 3 |
| A>G | 1 | 14 | 0 | 15 |

| Diagnostic Categories | Observed | Expected |
|---|---|---|
| 1. G>A mutations off the GYW motif at MC-2 sites | 8 | 2.50 |
| 2. C>T mutations off the WRC motif at MC-1 sites | 22 | 4.00 |
| 3. G>A mutations off the CG motif at MC-2 sites | 34 | 7.33 |
| 4. C>T mutations off the CG motif at MC-1 sites | 30 | 6.00 |
| 5. A>G mutations off WA motif at MC-2 sites | 14 | 3.50 |

CHI, SUARE  1.75449E-67

Figure 9

| Skin - "Malignant Melanoma" | | | | |
|---|---|---|---|---|
| Mutation | Location of mutations | | | |
| Type | MC-1 | MC-2 | MC-3 | Total |
| GYW/WRC sites (AID) | | | | |
| G>A | 1 | 2 | 0 | 3 |
| G>T | 2 | 0 | 0 | 2 |
| G>C | 0 | 0 | 0 | 0 |
| C>A | 0 | 0 | 0 | 0 |
| C>T | 3 | 0 | 2 | 5 |
| C>G | 0 | 0 | 0 | 0 |
| CG/CG sites (APOBEC3G) | | | | |
| G>A | 2 | 5 | 0 | 7 |
| G>T | 0 | 0 | 0 | 0 |
| G>C | 0 | 0 | 0 | 0 |
| C>A | 0 | 0 | 0 | 0 |
| C>T | 6 | 1 | 1 | 8 |
| C>G | 0 | 0 | 0 | 0 |
| WA sites | | | | |
| A>T | 0 | 1 | 0 | 1 |
| A>C | 0 | 1 | 0 | 1 |
| A>G | 0 | 4 | 0 | 4 |

| Diagnostic Categories | Observed | Expected |
|---|---|---|
| 1. G>A mutations off the GYW motif at MC-2 sites | 2 | 0.83 |
| 2. C>T mutations off the WRC motif at MC-1 sites | 3 | 0.50 |
| 3. G>A mutations off the CG motif at MC-2 sites | 5 | 1.17 |
| 4. C>T mutations off the CG motif at MC-1 sites | 6 | 1.17 |
| 5. A>G mutations off WA motif at MC-2 sites | 4 | 1.00 |
| | CHI, SUARE | 2.25977E-11 |

Figure 10

| Cervix – All Adenocarcinoma ||||
|---|---|---|---|---|
| Mutation | Location of mutations ||||
| Type | MC-1 | MC-2 | MC-3 | Total |
| GYW/WRC sites (AID) |||||
| G>A | 0 | 0 | 0 | 0 |
| G>T | 0 | 1 | 0 | 1 |
| G>C | 0 | 0 | 0 | 0 |
| C>A | 0 | 0 | 0 | 0 |
| C>T | 1 | 0 | 0 | 1 |
| C>G | 0 | 0 | 0 | 0 |
| CG/CG sites (APOBEC3G) |||||
| G>A | 0 | 3 | 0 | 3 |
| G>T | 0 | 0 | 0 | 0 |
| G>C | 0 | 0 | 0 | 0 |
| C>A | 0 | 0 | 0 | 0 |
| C>T | 5 | 0 | 0 | 5 |
| C>G | 0 | 0 | 0 | 0 |
| TG/CA (APOBEC1) |||||
| G>A | 0 | 0 | 0 | 0 |
| G>T | 0 | 0 | 0 | 0 |
| G>C | 0 | 0 | 0 | 0 |
| C>A | 0 | 0 | 0 | 0 |
| C>T | 0 | 0 | 0 | 0 |
| C>G | 0 | 0 | 0 | 0 |
| WA sites |||||
| A>T | 0 | 1 | 0 | 1 |
| A>C | 0 | 0 | 0 | 0 |
| A>G | 0 | 0 | 0 | 0 |

| Diagnostic Categories | Observed | Expected |
|---|---|---|
| 1. G>A mutations off the GYW motif at MC-2 sites | 0 | 0.17 |
| 2. C>T mutations off the WRC motif at MC-1 sites | 1 | 0.17 |
| 3. G>A mutations off the CG motif at MC-2 sites | 3 | 0.50 |
| 4. C>T mutations off the CG motif at MC-1 sites | 5 | 0.83 |
| 5. A>G mutations off WA motif at MC-2 sites | 0 | 0.17 |

CHI, SUARE  1.21287E-07

Figure 11

| Cervix - Adenocarcinoma, NOS | | | | |
|---|---|---|---|---|
| Mutation | Location of mutations | | | |
| Type | MC-1 | MC-2 | MC-3 | Total |
| GYW/WRC sites (AID) | | | | |
| G>A | 0 | 2 | 0 | 2 |
| G>T | 0 | 1 | 0 | 1 |
| G>C | 0 | 0 | 0 | 0 |
| C>A | 0 | 0 | 0 | 0 |
| C>T | 1 | 0 | 0 | 1 |
| C>G | 0 | 0 | 0 | 0 |
| CG/CG sites (APOBEC3G) | | | | |
| G>A | 0 | 1 | 0 | 1 |
| G>T | 0 | 0 | 1 | 1 |
| G>C | 0 | 0 | 0 | 0 |
| C>A | 0 | 0 | 0 | 0 |
| C>T | 1 | 0 | 0 | 1 |
| C>G | 0 | 0 | 0 | 0 |
| WA sites | | | | |
| A>T | 0 | 0 | 0 | 0 |
| A>C | 0 | 0 | 0 | 0 |
| A>G | 1 | 0 | 0 | 1 |

| Diagnostic Categories | Observed | Expected |
|---|---|---|
| 1. G>A mutations off the GYW motif at MC-2 sites | 2 | 0.50 |
| 2. C>T mutations off the WRC motif at MC-1 sites | 1 | 0.17 |
| 3. G>A mutations off the CG motif at MC-2 sites | 1 | 0.17 |
| 4. C>T mutations off the CG motif at MC-1 sites | 1 | 0.17 |
| 5. A>G mutations off WA motif at MC-2 sites | 0 | 0.17 |

CHI, SUARE  0.001793999

Figure 12

Breast - PIK3CA *(n = 105)*

| Mutation Type | Location of mutations | | | |
|---|---|---|---|---|
| | MC-1 | MC-2 | MC-3 | Total |
| GYW/WRC sites (AID) | | | | |
| G>A | 0 | 12 | 0 | 12 |
| G>T | 0 | 1 | 2 | 3 |
| G>C | 0 | 0 | 1 | 1 |
| C>A | 8 | 0 | 0 | 8 |
| C>T | 2 | 0 | 0 | 2 |
| C>G | 0 | 0 | 0 | 0 |
| CG/CG sites (APOBEC3G) | | | | |
| G>A | 3 | 22 | 0 | 25 |
| G>T | 0 | 3 | 0 | 3 |
| G>C | 0 | 1 | 0 | 1 |
| C>A | 1 | 0 | 0 | 1 |
| C>T | 3 | 0 | 2 | 5 |
| C>G | 0 | 0 | 0 | 0 |
| WA sites | | | | |
| A>T | 1 | 1 | 0 | 2 |
| A>C | 0 | 0 | 0 | 0 |
| A>G | 7 | 3 | 0 | 10 |

Breast - PIK3CA *(n = 105)*

| Diagnostic Categories | Observed | Expected |
|---|---|---|
| 1. G>A mutations off the GYW motif at MC-2 sites | 12 | 2.17 |
| 2. C>T mutations off the WRC motif at MC-1 sites | 2 | 1.67 |
| 3. G>A mutations off the CG motif at MC-2 sites | 22 | 4.83 |
| 4. C>T mutations off the CG motif at MC-1 sites | 3 | 0.67 |
| 5. A>G mutations off WA motif at MC-2 sites | 3 | 2.00 |

CHI, SUARE 8.662E-24

Figure 13

| Haematopoietic and lymphoid tissue – TET2 (n = 615) | | | | |
|---|---|---|---|---|
| Mutation Type | Location of mutations | | | |
| | MC-1 | MC-2 | MC-3 | Total |
| GYW/WRC sites (AID) | | | | |
| G>A | 4 | 11 | 2 | 17 |
| G>T | 10 | 3 | 0 | 13 |
| G>C | 0 | 1 | 1 | 2 |
| C>A | 1 | 1 | 5 | 7 |
| C>T | 72 | 6 | 0 | 78 |
| C>G | 1 | 1 | 7 | 9 |
| CG/CG sites (APOBEC3G) | | | | |
| G>A | 2 | 7 | 1 | 10 |
| G>T | 7 | 0 | 0 | 7 |
| G>C | 0 | 1 | 0 | 1 |
| C>A | 1 | 0 | 0 | 1 |
| C>T | 84 | 1 | 3 | 88 |
| C>G | 0 | 1 | 3 | 4 |
| TG/CA (APOBEC1) | | | | |
| G>A | 5 | 16 | 1 | 22 |
| G>T | 16 | 4 | 0 | 20 |
| G>C | 3 | 3 | 0 | 6 |
| C>A | 1 | 13 | 2 | 16 |
| C>T | 147 | 7 | 1 | 155 |
| C>G | 3 | 19 | 3 | 25 |
| WA sites | | | | |
| A>T | 4 | 0 | 0 | 4 |
| A>C | 1 | 2 | 0 | 3 |
| A>G | 13 | 2 | 1 | 16 |

| Diagnostic Categories | Observed | Expected |
|---|---|---|
| 1. G>A mutations off the GYW motif at MC-2 sites | 11 | 4.83 |
| 2. C>T mutations off the WRC motif at MC-1 sites | 72 | 13.67 |
| 3. G>A mutations off the CG motif at MC-2 sites | 7 | 2.83 |
| 4. C>T mutations off the CG motif at MC-1 sites | 84 | 14.50 |
| 5. A>G mutations off WA motif at MC-2 sites | 2 | 3.67 |

CHI, SUARE 7.42E-128

TSM Test for AID/APO activity

| Mutation Type | Location of mutations | | | |
|---|---|---|---|---|
| | MC-1 | MC-2 | MC-3 | Total |
| GYW/WRC sites (AID) | | | | |
| G>A | 0 | 1 | 0 | 1 |
| G>T | 1 | 0 | 0 | 1 |
| G>C | 0 | 0 | 0 | 0 |
| C>A | 0 | 0 | 0 | 0 |
| C>T | 2 | 0 | 2 | 4 |
| C>G | 0 | 1 | 0 | 1 |
| CG/CG sites (APOBEC3G) | | | | |
| G>A | 0 | 2 | 0 | 2 |
| G>T | 0 | 0 | 0 | 0 |
| G>C | 0 | 0 | 0 | 0 |
| C>A | 0 | 0 | 0 | 0 |
| C>T | 0 | 0 | 0 | 0 |
| C>G | 0 | 0 | 0 | 0 |
| WA sites | | | | |
| A>T | 0 | 0 | 0 | 0 |
| A>C | 0 | 0 | 0 | 0 |
| A>G | 0 | 0 | 0 | 0 |

| | |
|---|---|
| Sample: | PD3185a |
| Mutations (n): | 11 |
| TSM Activation: | AID/APO3G POSITIVE |
| Significance (p value): | 0.00083897 |

| Diagnostic Categories | Observed | Expected |
|---|---|---|
| 1. G>A mutations off the GYW motif at MC-2 sites | 1.00 | 0.333 |
| 2. C>T mutations off the WRC motif at MC-1 sites | 2.00 | 0.500 |
| 3. G>A mutations off the CG motif at MC-2 sites | 2.00 | 0.333 |
| 4. C>T mutations off the CG motif at MC-1 sites | 0.00 | 0.000 |
| 5. A>G mutations off WA motif at MC-2 sites | 0.00 | 0.000 |

B.

TSM Test for AID/APO activity

| Mutation Type | Location of mutations | | | |
|---|---|---|---|---|
| | MC-1 | MC-2 | MC-3 | Total |
| GYW/WRC sites (AID) | | | | |
| G>A | 0 | 0 | 0 | 0 |
| G>T | 0 | 0 | 0 | 0 |
| G>C | 0 | 0 | 1 | 1 |
| C>A | 0 | 0 | 0 | 0 |
| C>T | 0 | 0 | 1 | 1 |
| C>G | 0 | 0 | 0 | 0 |
| CG/CG sites (APOBEC3G) | | | | |
| G>A | 0 | 0 | 0 | 0 |
| G>T | 0 | 0 | 0 | 0 |
| G>C | 0 | 0 | 0 | 0 |
| C>A | 0 | 0 | 0 | 0 |
| C>T | 0 | 1 | 1 | 2 |
| C>G | 0 | 0 | 0 | 0 |
| WA sites | | | | |
| A>T | 0 | 1 | 0 | 1 |
| A>C | 0 | 0 | 1 | 1 |
| A>G | 0 | 0 | 0 | 0 |
| A>C | 0 | 0 | 0 | 0 |
| A>G | 0 | 0 | 0 | 0 |

| | |
|---|---|
| Sample: | PD3181a |
| Mutations (n): | 23 |
| TSM Activation: | NEGATIVE |
| Significance (p value): | |

| Diagnostic Categories | Observed | Expected |
|---|---|---|
| 1. G>A mutations off the GYW motif at MC-2 sites | 0.00 | 0.000 |
| 2. C>T mutations off the WRC motif at MC-1 sites | 0.00 | 0.000 |
| 3. G>A mutations off the CG motif at MC-2 sites | 0.00 | 0.000 |
| 4. C>T mutations off the CG motif at MC-1 sites | 0.00 | 0.167 |
| 5. A>G mutations off WA motif at MC-2 sites | 0.00 | 0.167 |

TSM Test for AID/APO activity

| Mutation Type | Location of mutations | | | |
|---|---|---|---|---|
| | MC-1 | MC-2 | MC-3 | Total |
| GYW/WRC sites (AID) | | | | |
| G>A | 0 | 1 | 0 | 1 |
| G>T | 0 | 1 | 0 | 1 |
| G>C | 1 | 0 | 0 | 1 |
| C>A | 0 | 0 | 0 | 0 |
| C>T | 2 | 0 | 1 | 3 |
| C>G | 0 | 0 | 0 | 0 |
| CG/CG sites (APOBEC3G) | | | | |
| G>A | 0 | 1 | 1 | 2 |
| G>T | 0 | 1 | 0 | 1 |
| G>C | 0 | 0 | 0 | 0 |
| C>A | 0 | 0 | 0 | 0 |
| C>T | 2 | 0 | 0 | 2 |
| C>G | 0 | 0 | 0 | 0 |
| WA sites | | | | |
| A>T | 1 | 0 | 0 | 1 |
| A>C | 0 | 0 | 1 | 1 |
| A>G | 0 | 2 | 0 | 2 |

Sample: WA7
Mutations (n): 41
TSM Activation: POSITIVE
Significance (p value): 0.000126626

| Diagnostic Categories | Observed | Expected |
|---|---|---|
| 1. G>A mutations off the GYW motif at MC-2 sites | 1.00 | 0.500 |
| 2. C>T mutations off the WRC motif at MC-1 sites | 2.00 | 0.333 |
| 3. G>A mutations off the CG motif at MC-2 sites | 1.00 | 0.333 |
| 4. C>T mutations off the CG motif at MC-1 sites | 2.00 | 0.333 |
| 5. A>G mutations off WA motif at MC-2 sites | 2.00 | 0.500 |

Comments:

B.

TSM Test for AID/APO activity

| Mutation Type | Location of mutations | | | |
|---|---|---|---|---|
| | MC-1 | MC-2 | MC-3 | Total |
| GYW/WRC sites (AID) | | | | |
| G>A | 1 | 1 | 3 | 5 |
| G>T | 2 | 0 | 1 | 3 |
| G>C | 0 | 0 | 0 | 0 |
| C>A | 0 | 0 | 0 | 0 |
| C>T | 3 | 0 | 4 | 7 |
| C>G | 1 | 0 | 0 | 1 |
| CG/CG sites (APOBEC3G) | | | | |
| G>A | 7 | 5 | 4 | 16 |
| G>T | 0 | 0 | 0 | 0 |
| G>C | 0 | 0 | 0 | 0 |
| C>A | 0 | 0 | 0 | 0 |
| C>T | 3 | 9 | 2 | 14 |
| C>G | 0 | 1 | 0 | 1 |
| WA sites | | | | |
| A>T | 2 | 1 | 0 | 3 |
| A>C | 0 | 1 | 0 | 1 |
| A>G | 0 | 1 | 0 | 1 |

Sample: WA26
Mutations (n): 115
TSM Activation: POSITIVE
Significance (p value): 0.010396508

| Diagnostic Categories | Observed | Expected |
|---|---|---|
| 1. G>A mutations off the GYW motif at MC-2 sites | 1.00 | 0.667 |
| 2. C>T mutations off the WRC motif at MC-1 sites | 3.00 | 0.667 |
| 3. G>A mutations off the CG motif at MC-2 sites | 5.00 | 2.000 |
| 4. C>T mutations off the CG motif at MC-1 sites | 3.00 | 2.167 |
| 5. A>G mutations off WA motif at MC-2 sites | 1.00 | 0.833 |

Comments:

Figure 15B

C.
TSM Test for AID/APO activity

| Mutation Type | Location of mutations | | | |
|---|---|---|---|---|
| | MC-1 | MC-2 | MC-3 | Total |
| GYW/WRC sites (AID) | | | | |
| G>A | 0 | 1 | 1 | 2 |
| G>T | 1 | 0 | 0 | 1 |
| G>C | 0 | 0 | 0 | 0 |
| C>A | 0 | 0 | 0 | 0 |
| C>T | 1 | 1 | 1 | 3 |
| C>G | 0 | 0 | 0 | 0 |
| CG/CG sites (APOBEC3G) | | | | |
| G>A | 1 | 5 | 1 | 7 |
| G>T | 5 | 0 | 0 | 5 |
| G>C | 0 | 0 | 0 | 0 |
| C>A | 0 | 0 | 0 | 0 |
| C>T | 6 | 2 | 6 | 14 |
| C>G | 0 | 0 | 0 | 0 |
| WA sites | | | | |
| A>T | 1 | 0 | 0 | 1 |
| A>C | 0 | 1 | 0 | 1 |
| A>G | 0 | 1 | 0 | 1 |

Sample: PR-09-3421
Mutations (n): 49
TSM Activation: POSITIVE
Significance (p value): 5.10206E-05

| Diagnostic Categories | Observed | Expected |
|---|---|---|
| 1. G>A mutations off the GYW motif at MC-2 sites | 1.00 | 0.333 |
| 2. C>T mutations off the WRC motif at MC-1 sites | 1.00 | 0.333 |
| 3. G>A mutations off the CG motif at MC-2 sites | 5.00 | 1.833 |
| 4. C>T mutations off the CG motif at MC-1 sites | 6.00 | 1.333 |
| 5. A>G mutations off WA motif at MC-2 sites | 1.00 | 0.500 |

Comments:
Also note significant numbers of G>T at MC-1
and C>T at MC-3.

Suggests that another APO-family deaminase
with a different codon-bias preference
might be active in this patient.

D.
TSM Test for AID/APO activity

| Mutation Type | Location of mutations | | | |
|---|---|---|---|---|
| | MC-1 | MC-2 | MC-3 | Total |
| GYW/WRC sites (AID) | | | | |
| G>A | 2 | 1 | 1 | 4 |
| G>T | 0 | 0 | 0 | 0 |
| G>C | 0 | 0 | 0 | 0 |
| C>A | 1 | 0 | 0 | 1 |
| C>T | 0 | 1 | 0 | 1 |
| C>G | 0 | 0 | 1 | 1 |
| CG/CG sites (APOBEC3G) | | | | |
| G>A | 3 | 2 | 1 | 6 |
| G>T | 0 | 0 | 0 | 0 |
| G>C | 0 | 0 | 0 | 0 |
| C>A | 0 | 1 | 0 | 1 |
| C>T | 0 | 3 | 4 | 7 |
| C>G | 0 | 0 | 0 | 0 |
| WA sites | | | | |
| A>T | 0 | 0 | 0 | 0 |
| A>C | 0 | 0 | 0 | 0 |
| A>G | 1 | 1 | 0 | 2 |

Sample: PR-2762
Mutations (n): 42
TSM Activation: NEGATIVE
Significance (p value): 0.346518269

| Diagnostic Categories | Observed | Expected |
|---|---|---|
| 1. G>A mutations off the GYW motif at MC-2 sites | 1.00 | 0.500 |
| 2. C>T mutations off the WRC motif at MC-1 sites | 0.00 | 0.333 |
| 3. G>A mutations off the CG motif at MC-2 sites | 2.00 | 0.833 |
| 4. C>T mutations off the CG motif at MC-1 sites | 0.00 | 0.667 |
| 5. A>G mutations off WA motif at MC-2 sites | 1.00 | 0.333 |

Comments:

Deaminase (high G>A/C>T) activity may be due to
one or more other members of the APOBEC
family of deaminases.

Figure 16

Source: Sample Name B10, COSMIC database

| Mutation Type | Location of mutations | | | |
|---|---|---|---|---|
| | MC-1 | MC-2 | MC-3 | Total |
| GA sites (APOBEC3H) | | | | |
| G>A | 19 | 2 | 3 | 24 |
| G>T | 4 | 0 | 0 | 4 |
| G>C | 5 | 4 | 1 | 10 |
| Total | 28 | 6 | 4 | 38 |

Bladder Carcinoma, grade 2
Male, 52
Remark - Discovery (pre-treatment)

| | |
|---|---|
| Sample: | 0 |
| Mutations ($n$): | 88 (38/88 occur at GA sites) |
| TSM Activation for APOBEC3H: | POSITIVE |
| Significance ($p$ value): | 6.589E-11 |

| Diagnostic Test for APOBEC3H | Observed | Expected |
|---|---|---|
| 1. G>A mutations off the GA motif at MC-1 sites | 19 | 4.222 |
| 2. G>A mutations off the GA motif at MC-2 sites | 2 | 4.222 |
| 3. G>A mutations off the GA motif at MC-3 sites | 3 | 4.222 |
| 4. G>T mutations off the GA motif at MC-1 sites | 4 | 4.222 |
| 5. G>T mutations off the GA motif at MC-2 sites | 0 | 4.222 |
| 6. G>T mutations off the GA motif at MC-3 sites | 0 | 4.222 |
| 7. G>C mutations off the GA motif at MC-1 sites | 5 | 4.222 |
| 8. G>C mutations off the GA motif at MC-2 sites | 4 | 4.222 |
| 7. G>C mutations off the GA motif at MC-3 sites | 1 | 4.222 |

TSM Test for APOBEC3G activity (using CC dinucleotide)

Samples B2, B5, B8-10, B13, B15, B20 COSMIC (v.66)

| Mutation Type | Location of mutations | | | |
|---|---|---|---|---|
| | MC-1 | MC-2 | MC-3 | Total |
| CC sites (APOBEC3G) | | | | |
| C>A | 2 | 0 | 4 | 6 |
| C>G | 2 | 2 | 3 | 7 |
| C>T | 9 | 1 | 2 | 12 |
| Total | 13 | 3 | 9 | 25 |

Bladder Carcinoma

Remark - All discovery (pre-treatment)

| | |
|---|---|
| Sample: | 8 samples (pre-treatment) |
| Mutations (n): | 473 |
| TSM Activation for APOBEC3H: | POSITIVE (p< 0.05) |
| Significance (p value): | 0.01343184 |

| Diagnostic Test for APOBEC3H | Observed | Expected |
|---|---|---|
| 1. C>A mutations off the CC motif at MC-1 sites | 2 | 2.778 |
| 2. C>A mutations off the CC motif at MC-2 sites | 0 | 2.778 |
| 3. C>A mutations off the CC motif at MC-3 sites | 4 | 2.778 |
| 4. C>G mutations off the CC motif at MC-1 sites | 2 | 2.778 |
| 5. C>G mutations off the CC motif at MC-2 sites | 2 | 2.778 |
| 6. C>G mutations off the GA motif at MC-3 sites | 3 | 2.778 |
| 7. C>T mutations off the CC motif at MC-1 sites | 9 | 2.778 |
| 8. C>T mutations off the CC motif at MC-2 sites | 1 | 2.778 |
| 7. C>T mutations off the CC motif at MC-3 sites | 2 | 2.778 |

B.

TSM Test for APOBEC3G activity (using CC dinucleotide motif)

Source: Sample Name B13, COSMIC database (v.66)

| Mutation Type | Location of mutations | | | |
|---|---|---|---|---|
| | MC-1 | MC-2 | MC-3 | Total |
| CC sites (APOBEC3G) | | | | |
| C>A | 0 | 0 | 0 | 0 |
| C>G | 0 | 0 | 0 | 0 |
| C>T | 2 | 0 | 0 | 2 |
| Total | 2 | 0 | 0 | 2 |

| | |
|---|---|
| Sample: | 0 |
| Mutations (n): | 39 |
| TSM Activation for APOBEC3H: | POSITIVE (p<0.05) |
| Probability that mutations are random: | =(1/9)*(1/9) = 0.0123 |

Bladder Carcinoma, grade 2

Male, 64

Remark - Discovery (pre-treatment)

METHODS FOR DETERMINING THE CAUSE OF SOMATIC MUTAGENESIS

FIELD OF THE INVENTION

This invention relates generally to methods for determining the likelihood that targeted somatic mutagenesis of a nucleic acid molecule by a mutagenic agent has occurred, and the likelihood that a mutagenic agent is a cause of targeted somatic mutagenesis of a nucleic acid molecule. The invention further relates to methods for diagnosing cancer in a subject and/or determining the likelihood that a subject has or will develop cancer, and methods for treating subjects diagnosed with cancer or determined to be likely to have or to develop cancer. In further aspects, the invention relates to methods for identifying motifs in nucleic acid molecules that are recognized or targeted by mutagenic agents.

RELATED APPLICATIONS

This application claims priority to Australian Provisional Application No. 2012904826, entitled "Method for the diagnosis of disease associated with somatic mutagenesis", filed on 5 Nov. 2012; Australian Provisional Application No. 2012904940, entitled "Database system and method for the diagnosis of disease associated with somatic mutagenesis", filed on 13 Nov. 2012; and Australian Provisional Application No. 2013901253, entitled "Method for the diagnosis of disease associated with mutagenesis using small numbers of somatic mutations", filed on 12 Apr. 2013. The subject matter of Australian Provisional Application Nos. 2012904826, 2012904940 and 2013901253 is incorporated herein by reference in its entirety.

BACKGROUND OF THE INVENTION

The progression of normal cells to cancer cells can be influenced by a variety of factors, including changes in the immune system, hormonal status, gene expression and signalling between tissues. A particularly important factor in cancer progression is somatic mutation, which plays a role in cancers of most, if not all, tissue types.

The accumulation of somatic mutations in various genes appears directly related to cancer progression. This has been demonstrated using various animal models in which an increase in somatic mutagenesis resulting from, for example, impaired DNA polymerase proofreading or DNA repair, was associated with accelerated tumor progression (see e.g. Venkatesan et al. (2007). Mol. Cell. Biol. 27: 7669-7682; and Albertson (2009) Proc. Natl. Acad. Sci. U.S.A. 106, 17101-17104). Increased somatic mutagenesis of various genes has also been associated with a variety of cancers. For example, somatic mutations in the TP53 gene are one of the most frequent alterations in human cancers. Somatic TP53 mutations occur in almost every type of cancer at rates from 38%-50% in ovarian, esophageal, colorectal, head and neck, larynx, and lung cancers to about 5% in primary leukemia, sarcoma, testicular cancer, malignant melanoma, and cervical cancer, and advanced stage or aggressive cancer subtypes (such as triple negative or HER2-amplified breast cancers) are associated with an increased frequency of somatic mutations in TP53 (reviewed in Olivier et al. (2010) Cold Spring Harb Perspect Biol 2:a001008). Other genes associated with cancer that accumulate somatic mutations include, for example, BRAF, HRAS, KRAS2 and NRAS, although over 25000 genes are now included in COSMIC, the online database of somatically acquired mutations found in human cancer.

Somatic mutagenesis can be caused by environmental factors, such as cigarette smoke, UV light and radiation, and/or biological factors or processes, such as chromosome translocation, DNA mis-repair or non-repair, and enzyme-initiated somatic hypermutation (SHM). Determining the cause and extent of somatic mutagenesis in cells can not only assist in diagnosing conditions associated with somatic mutagenesis or predicting the risk of developing such conditions, but can also assist in developing the most appropriate treatment or prevention protocols. Thus, there is a need for accurate methods for determining the presence of somatic mutagenesis and identifying which mutagenic agent or agents are responsible for somatic mutagenesis in a subject.

SUMMARY OF THE INVENTION

The present invention is predicated in part on the determination that there is a bias towards somatic mutagenesis by various mutagenic agents at motifs when the motifs are present in a particular codon context within the nucleic acid molecule. Thus, while it was previously understood that some mutagenic agents target motifs, as described herein mutagenesis at these motifs occurs predominantly when the motifs are within a particular codon context, a process termed herein targeted somatic mutagenesis. By identifying this additional requirement for the codon context of the motif, the present inventors have developed methods for determining the likelihood that this type of targeted somatic mutagenesis has occurred, and the likelihood that one or more particular mutagenic agents are the cause of the targeted somatic mutagenesis. Generalized methods for identifying motifs targeted by mutagenic agents through assessing instances of targeted somatic mutation have also been developed and are described herein.

As the accumulation of somatic mutations is associated with the development and progression of cancer, methods for diagnosing cancer in a subject and determining the likelihood that a subject has or will develop cancer have also been developed. By identifying the causative mutagenic agent and/or diagnosing the cancer or likelihood of developing cancer, appropriate and specific treatment protocols can be developed to inhibit or reduce the activity of the mutagenic agent, and/or treat or prevent the cancer.

Thus, in one aspect, the present invention is directed to methods for detecting or determining the likelihood that targeted somatic mutagenesis of a nucleic acid molecule by a mutagenic agent has occurred, comprising analysing the sequence of the nucleic acid molecule to determine the codon context of mutations of a mutation type at one or more motifs, wherein a determination that targeted somatic mutagenesis has been detected or is likely to have occurred is made when there is a higher than expected percentage or number of the mutations at one position in codons in the nucleic acid molecule.

Generally, the expected percentage or number of mutations is calculated by assuming that mutations occur independently of codon context. In some embodiments, the expected percentage of mutations is approximately 11% or 17%, and/or the expected number of mutations is approximately 1 of every 9 mutations or 1 of every 6 mutations. In some examples, the percentage of mutations is observed to be at least 30%, 35%, 40%, 45%, 50%, 55%, 60%, 65%, 70%, 80%, 85%, 90%, 95% or more.

The methods for determining whether targeted somatic mutagenesis has occurred can further comprise determining which mutagenic agent is a likely cause of the targeted somatic mutagenesis. The mutagenic agent can be selected from, for example, aflatoxin, 4-aminobiphenyl, aristolochic acids, arsenic compounds, asbestos, azathioprine, benzene, benzidine, beryllium and beryllium compounds, 1,3-butadiene, 1,4-butanediol dimethylsulfonate, cadmium and cadmium compounds, chlorambucil, 1-(2-chloroethyl)-3-(4-methylcyclohexyl)-1-nitrosourea (MeCCNU), bis (chloromethyl) ether and technical-grade chloromethyl methyl ether, chromium hexavalent compounds, coal tar pitches, coal tars, coke oven emissions, cyclophosphamide, cyclosporin A, diethylstilbestrol (DES), erionite, ethylene oxide, formaldehyde, melphalan, methoxsalen with ultraviolet A therapy (PUVA), mustard gas, 2-naphthylamine, neutrons, nickel compounds, radon, crystalline silica (respirable size), solar radiation, soot, strong inorganic acid mists containing sulfuric acid, tamoxifen, 2,3,7,8-tetrachlorodibenzo-p-dioxin (TCDD), thiotepa, thorium dioxide, tobacco smoke, vinyl chloride, ultraviolet radiation, wood dust, X-radiation, gamma radiation, activation-induced cytidine deaminase (AID), an apolipoprotein B mRNA-editing enzyme catalytic polypeptide-like (APOBEC) cytidine deaminase, and error-prone DNA polymerases. In some examples, the APOBEC cytidine deaminase is selected from among APOBEC1, APOBEC3A, APOBEC3B, APOBEC3C, APOBEC3D, APOBEC3F, APOBEC3G and APOBEC3H.

In particular embodiments where the mutagenic agent is selected from among AID, APOBEC1, APOBEC3G, APOBEC3H and aflatoxin, a determination that AID is a likely cause of targeted somatic mutagenesis is made if the number or percentage of observed G>A mutations in GYW motifs at the second position in codons (MC-2 sites) in the non-transcribed strand of the nucleic acid molecule is higher than expected; a determination that AID is a likely cause of targeted somatic mutagenesis is made if the number or percentage of observed C>T mutations in WRC motifs at the first position in codons (MC-1 sites) in the non-transcribed strand of the nucleic acid molecule is higher than expected; a determination that APOBEC3G is a likely cause of targeted somatic mutagenesis is made if the number or percentage of observed. G>A mutations in CG motifs at MC-2 sites in the non-transcribed strand of the nucleic acid molecule is higher than expected; a determination that APOBEC3G is a likely cause of targeted somatic mutagenesis is made if there is a higher than expected number or percentage of observed C>T mutations in CG motifs at MC-1 sites in the non-transcribed strand of the nucleic acid molecule is higher than expected; a determination that APOBEC3G is a likely cause of targeted somatic mutagenesis is made if there is a higher than expected number or percentage of observed C>T mutations in CC motifs at MC-1 sites in the non-transcribed strand of the nucleic acid molecule is higher than expected; a determination that APOBEC3H is a likely cause of targeted somatic mutagenesis is made if there is a higher than expected number or percentage of observed G>A mutations in GA motifs at MC-1 sites in the non-transcribed strand of the nucleic acid molecule is higher than expected; a determination that APOBEC1 is a likely cause of targeted somatic mutagenesis is made if the number or percentage of observed C>T mutations in CA motifs at MC-1 sites in the non-transcribed strand of the nucleic acid molecule is higher than expected; a determination that APOBEC1 is a likely cause of targeted somatic mutagenesis is made if the number or percentage of observed G>A mutations in TG motifs at MC-2 sites in the non-transcribed strand of the nucleic acid molecule is higher than expected; and a determination that aflatoxin is a likely cause of targeted somatic mutagenesis is made if the number or percentage of observed G>T mutations in GG motifs at MC-3 sites in the non-transcribed strand of the nucleic acid molecule is higher than expected; wherein the nucleic acid molecule is from a biological sample from a subject.

Other embodiments of the methods for determining whether targeted somatic mutagenesis has occurred further comprise determining whether an AID-associated mutation process is a likely cause of the targeted somatic mutagenesis. For example, a determination that an AID-associated mutation process is a likely cause of targeted somatic mutagenesis is made if the number or percentage of observed A>G mutations in WA motifs at MC-2 sites, G>A mutations in GYW motifs at MC-2 sites, or C>T mutations in WRC motifs at MC-1 sites, in the non-transcribed strand of the nucleic acid molecule is higher than expected.

In particular examples of the methods of the present invention, if AID is determined to be a likely cause of targeted somatic mutagenesis, the methods further comprising administering an AID inhibitor to the subject; if APOBEC3G is determined to be a likely cause of targeted somatic mutagenesis, further comprising administering an APOBEC3G inhibitor to the subject; if APOBEC3H is determined to be a likely cause of targeted somatic mutagenesis, further comprising administering an APOBEC3G inhibitor to the subject; or if APOBEC1 is determined to be a likely cause of targeted somatic mutagenesis, further comprising administering an APOBEC1 inhibitor to the subject.

In further embodiments, the methods also comprise diagnosing cancer in the subject or determining the likelihood that the subject will develop cancer if it is determined that targeted somatic mutagenesis has occurred and/or a mutagenic agent is the likely cause of targeted somatic mutagenesis.

In other aspects, the present invention is directed to methods for determining the likelihood that a subject has or will develop cancer, comprising analysing a nucleic acid molecule from a biological sample from the subject to detect whether targeted somatic mutagenesis by one or more mutagenic agents has occurred, and determining that the subject is likely to have or to develop cancer when targeted somatic mutagenesis has occurred.

In one example, targeted somatic mutagenesis is detected when: the number or percentage of observed G to A mutations in GYW motifs at MC-2 sites in the non-transcribed strand of the nucleic acid molecule is higher than expected; the number or percentage of observed C>T mutations in WRC motifs at MC-1 sites in the non-transcribed strand of the nucleic acid molecule is higher than expected; the number or percentage of observed G>A mutations in CG motifs at MC-2 sites in the non-transcribed strand of the nucleic acid molecule is higher than expected; the number or percentage of observed C>T mutations in CG motifs at MC-1 sites in the non-transcribed strand of the nucleic acid molecule is higher than expected; the number or percentage of observed C>T mutations in CA motifs at MC-1 sites in the non-transcribed strand of the nucleic acid molecule is higher than expected; the number or percentage of observed G>A mutations in GA motifs at MC-1 sites in the non-transcribed strand of the nucleic acid molecule is higher than expected; the number or percentage of observed G>A mutations in TG motifs at MC-2 sites in the non-transcribed strand of the nucleic acid molecule is higher than expected; the number or percentage of observed G>T mutations in G<u>G</u> motifs at MC-3 sites in the non-transcribed strand of the nucleic acid molecule is higher than expected; the number or percentage of observed C>T mutations in <u>C</u>C motifs at MC-1 sites in the non-transcribed strand of the nucleic acid molecule is higher than expected; or the number or percentage of observed A>G mutations in W<u>A</u> motifs at MC-2 sites in the non-transcribed strand of the nucleic acid molecule is higher than expected.

In particular examples, the mutagenic agent is determined to be AID if the number or percentage of observed G>A mutations in <u>G</u>YW motifs at MC-2 sites or C>T mutations in WR<u>C</u> motifs at MC-1 sites in the non-transcribed strand of the nucleic acid molecule is higher than expected; APOBEC3G if the number or percentage of observed G>A mutations in C<u>G</u> motifs at MC-2 sites, C>T mutations in <u>C</u>G motifs at MC-1 sites or C>T mutations in <u>C</u>C motifs at MC-1 sites in the non-transcribed strand of the nucleic acid molecule is higher than expected; APOBEC1 if the number or percentage of observed C>T mutations in <u>C</u>A motifs at MC-1 sites or G>A mutations in T<u>G</u> motifs at MC-2 sites in the non-transcribed strand of the nucleic acid molecule is higher than expected; APOBEC3H if the number or percentage of observed G>A mutations in G<u>A</u> motifs at MC-1 sites in the non-transcribed strand of the nucleic acid molecule is higher than expected; or aflatoxin if the number or percentage of observed G>T mutations in G<u>G</u> motifs at MC-3 sites in the non-transcribed strand of the nucleic acid molecule is higher than expected.

The biological sample may comprise breast, prostate, liver, colon, stomach, pancreatic, skin, thyroid, cervical, lymphoid, haematopoietic, bladder, lung, renal, rectal, ovarian, uterine, and head or neck tissue or cells, and, in some instances, the cancer is selected from among breast, prostate, liver, colon, stomach, pancreatic, skin, thyroid, cervical, lymphoid, haematopoietic, bladder, lung, renal, rectal, ovarian, uterine, and head and neck cancer. In particular examples, the cancer hepatocellular carcinoma, melanoma or adenoid cystic carcinoma.

In some embodiments of the present invention, if the sample comprises prostate tissue or cells, the subject is diagnosed with prostate cancer or determined to be likely to have or develop cancer. In other embodiments, if the sample comprises breast tissue or cells, the subject is diagnosed with breast cancer or determined to be likely to have or develop breast cancer.

The methods of the present invention may further include administering therapy to the subject, such as, for example, radiotherapy, surgery, chemotherapy, hormone ablation therapy, pro-apoptosis therapy and/or immunotherapy. In particular examples, the methods include administering an AID inhibitor; an APOBEC3G inhibitor; an APOBEC1 inhibitor and/or an APOBEC3H inhibitor to the subject.

In another aspect, the present invention is directed to methods for identifying a nucleic acid motif targeted by a mutagenic agent, comprising analysing the sequence of a nucleic acid molecule to identify somatic mutations of a mutation type known to be associated with the mutagenic agent; determining the codon context of the mutations to identify the preferred nucleotide position at which the mutations occur at a higher than expected frequency; and identifying the nucleotides flanking the mutations at the preferred nucleotide position so as to identify a motif that is common to the mutations.

The invention is also directed to methods for identifying a nucleic acid motif targeted by a mutagenic agent, comprising analysing the sequence of a nucleic acid molecule to identify somatic mutations in the nucleic acid molecule; identifying a mutation type that occurs at a preferred nucleotide position within a codon at a higher than expected frequency; and identifying the nucleotides flanking the mutation type at the preferred nucleotide position so as identify a motif that is common to the mutation type.

The mutation type can be selected from C>T, C>A, C>G, G>T, G>A, G>C, A>T, A>C, A>G, T>A, T>C and T>G mutations, and the preferred nucleotide position may be selected from among MC-1, MC-2 and MC-3.

In such methods, the expected frequency is calculated by assuming that mutations occur independently of codon context. For example, the expected frequency may be approximately 1 of every 9 mutations or 1 of every 6 mutations. In some embodiments, the mutation occurs at the preferred nucleotide position a least 30%, 35%, 40%, 45%, 50%, 55%, 60%, 65%, 70%, 80%, 85%, 90%, 95% or more of the time.

In some embodiments of the methods of the present invention, the non-transcribed strand of the nucleic acid molecule is analysed.

The mutagenic agent may be endogenous or exogenous to the cells from which the nucleic acid was obtained. For example, the mutagenic agent may be selected from among 4-aminobiphenyl, aristolochic acids, arsenic compounds, asbestos, azathioprine, benzene, benzidine, beryllium and beryllium compounds, 1,3-butadiene, 1,4-butanediol dimethylsulfonate, cadmium and cadmium compounds, chlorambucil, 1-(2-chloroethyl)-3-(4-methylcyclohexyl)-1-nitrosourea (MeCCNU), bis(chloromethyl) ether and technical-grade chloromethyl methyl ether, chromium hexavalent compounds, coal tar pitches, coal tars, coke oven emissions, cyclophosphamide, cyclosporin A, diethylstilbestrol (DES), erionite, ethylene oxide, formaldehyde, melphalan, methoxsalen with ultraviolet A therapy (PUVA), mustard gas, 2-naphthylamine, neutrons, nickel compounds, radon, crystalline silica (respirable size), solar radiation, soot, strong inorganic acid mists containing sulfuric acid, tamoxifen, 2,3,7,8-tetrachlorodibenzo-p-dioxin (TCDD), thiotepa, thorium dioxide, tobacco smoke, vinyl chloride, ultraviolet radiation, wood dust, X-radiation, gamma radiation, an APOBEC cytidine deaminase, and an error-prone DNA polymerase. In particular examples of the methods of the invention, the nucleic acid molecule or the cell from which the nucleic acid molecule was obtained is known to have been exposed to the mutagenic agent prior to analysis.

Embodiments of the methods of the invention may also comprise first isolating the nucleic acid molecule and/or sequencing all or a part of the nucleic acid molecule. The nucleic acid molecule can comprise all or part of a single gene or the cDNA of a single gene; or all or part of two or more genes or the cDNA of two or more genes. In some instances, the gene is a gene associated with cancer. For example, the gene may be selected from among TP53, PIK3CA, ERBB2, DIRAS3, TET2 and nitric oxide synthase (NOS) genes. In further embodiments, nucleic acid molecule that constitute the whole exome of a cell or the whole genome of a cell are analysed.

The invention is also directed to a kit, comprising a reagent for use in a methods described herein. The reagent may be selected from, for example, among a primer, dNTPs and polymerase.

In particular embodiments of the methods of the present invention, all or a part of the method is performed by a processing system.

BRIEF DESCRIPTION OF THE DRAWINGS

FIG. 2 is a schematic showing an exemplary process of analysis of nucleic acid molecules to determine whether targeted somatic mutagenesis by AID or AOPBEC3G has occurred.

FIG. 3 is a schematic showing an analysis performed to determine whether mutations occur at random or as a result of targeted somatic mutagenesis.

FIG. 4 shows the frequency and location within codons of mutations at GYW/WRC sites (AID), CG/CG sites (APOBEC3G), TG/CA sites (APOBEC1) and WA sites in the TP53 gene of nucleic acid obtained from subjects with cervical cancer, and statistical analysis of the occurrence of the mutations.

FIG. 5 shows the frequency and location within codons of mutations at GYW/WRC sites (AID), CG/CG sites (APOBEC3G), TG/CA sites (APOBEC1) and WA sites in the TP53 gene of nucleic acid obtained from subjects with colon adenocarcinoma, and statistical analysis of the occurrence of the mutations.

FIG. 6 shows the frequency and location within codons of mutations at GYW/WRC sites (AID), CG/CG sites (APOBEC3G), TG/CA sites (APOBEC1), WA sites, and G G sites (aflatoxin) in the TP53 gene of nucleic acid obtained from subjects with hepatocellular carcinoma, and statistical analysis of the occurrence of the mutations.

FIG. 7 shows the frequency and location within codons of mutations at GYW/WRC sites (AID), CG/CG sites (APOBEC3G), TG/CA sites (APOBEC1) and WA sites in the TP53 gene of nucleic acid obtained from subjects with pancreatic cancer, and statistical analysis of the occurrence of the mutations.

FIG. 8 shows the frequency and location within codons of mutations at GYW/WRC sites (AID), CG/CG sites (APOBEC3G), TG/CA sites (APOBEC1) and WA sites in the TP53 gene of nucleic acid obtained from subjects with prostate cancer, and statistical analysis of the occurrence of the mutations.

FIG. 9 shows the frequency and location within codons of mutations at GYW/WRC sites (AID), CG/CG sites (APOBEC3G) and WA sites in the TP53 gene of nucleic acid obtained from subjects with malignant melanoma, and statistical analysis of the occurrence of the mutations.

FIG. 10 shows the frequency and location within codons of mutations at GYW/WRC sites (AID), CG/CG sites (APOBEC3G), TG/CA sites (APOBEC1) and WA sites in the TP53 gene of nucleic acid obtained from subjects with cervical adenocarcinoma, and statistical analysis of the occurrence of the mutations.

FIG. 11 shows the frequency and location within codons of mutations at GYW/WRC sites (AID), CG/CG sites (APOBEC3G) and WA sites in the NOS gene of nucleic acid obtained from subjects with cervical adenocarcinoma, and statistical analysis of the occurrence of the mutations.

FIG. 12 shows the frequency and location within codons of mutations at GYW/WRC sites (AID), CG/CG sites (APOBEC3G) and WA sites in the PIK3CA gene of nucleic acid obtained from subjects with breast cancer, and statistical analysis of the occurrence of the mutations.

FIG. 13 shows the frequency and location within codons of mutations at GYW/WRC sites (AID), CG/CG sites (APOBEC3G), TG/CA sites (APOBEC1) and WA sites in the TET2 gene of nucleic acid obtained from subjects with haematopoietic and lymphoid cancer, and statistical analysis of the occurrence of the mutations.

FIG. 14 shows the frequency and location within codons of mutations at GYW/WRC sites (AID), CG/CG sites (APOBEC3G) and WA sites in the whole exome of tissue obtained from two subjects with adenoid cystic carcinoma, and statistical analysis of the occurrence of the mutations. (A) Subject PD3185a. (B) Subject PD3181a.

FIG. 15 shows the frequency and location within codons of mutations at GYW/WRC sites (AID), CG/CG sites (APOBEC3G) and WA sites in the whole exome of tissue obtained from four subjects with prostate carcinoma, and statistical analysis of the occurrence of the mutations. (A) Subject WA7. (B) Subject WA26. (C) Subject PR-09-3421. (D) Subject PR-2762.

FIG. 16 shows the frequency and location within codons of mutations at GA sites (APOBEC3H) in the whole exome of nucleic acid obtained from a subjects with bladder cancer, and statistical analysis of the occurrence of the mutations.

FIG. 17 shows the frequency and location within codons of mutations at CC sites (APOBEC3G) in the whole exome of nucleic acid obtained from 8 subjects with bladder cancer (A), and a single subject with bladder cancer (B), and statistical analysis of the occurrence of the mutations.

TABLE A

NUCLEOTIDE SYMBOLS

Figure 1:
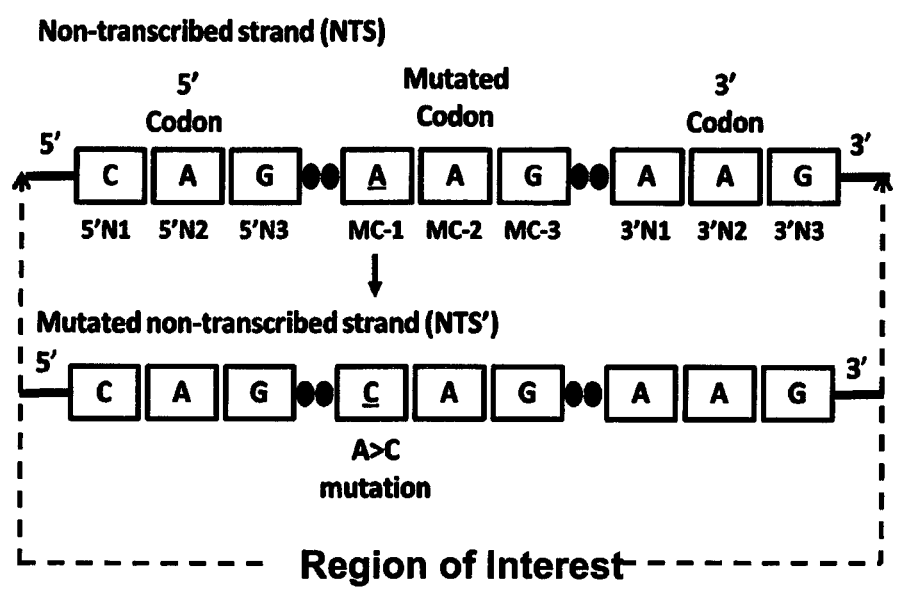
FIG. 1 is a schematic showing targeted somatic mutation in a region of interest on the non-transcribed strand of a nucleic acid molecule.

| SYMBOL | DESCRIPTION |
|---|---|
| A | Adenosine |
| C | Cytidine |
| G | Guanosine |
| T | Thymidine |
| U | Uridine |
| M | Amino (adenosine, cytosine) |
| K | Keto (guanosine, thymidine) |
| R | Purine (adenosine, guanosine) |
| Y | Pyrimidine (cytosine, thymidine) |
| W | Adenosine or cytosine |
| N | Any nucleotide |

DETAILED DESCRIPTION OF THE INVENTION

1. Definitions

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e. to at least one) of the grammatical object of the article. By way of example, "an element" means one element or more than one element.

The term "biological sample" as used herein refers to a sample that may be extracted, untreated, treated, diluted or concentrated from a subject or patient. Suitably, the biological sample is selected from any part of a patient's body, including, but not limited to hair, skin, nails, tissues or bodily fluids such as saliva and blood.

As used herein, the term "codon context" with reference to a mutation refers to the nucleotide position within a codon at which the mutation occurs. For the purposes of the present invention, the nucleotide positions within a mutated codon (MC; i.e. a codon containing the mutation) are annotated MC-1, MC-2 and MC-3, and refer to the first, second and third nucleotide positions, respectively, when the sequence of the codon is read 5' to 3'. Accordingly, the phrase "determining the codon context of a mutation" or similar phrase means determining at which nucleotide position within the mutated codon the mutation occurs, i.e. MC-1, MC-2 or MC-3.

Throughout this specification, unless the context requires otherwise, the words "comprise," "comprises" and "comprising" will be understood to imply the inclusion of a stated step or element or group of steps or elements but not the exclusion of any other step or element or group of steps or elements.

By "gene" is meant a unit of inheritance that occupies a specific locus on a genome and comprises transcriptional and/or translational regulatory sequences and/or a coding region and/or non-translated sequences (i.e., introns, 5' and 3' untranslated sequences).

As used herein, the term "likelihood" is used as a measure of whether targeted somatic mutagenesis has occurred, whether a particular mutagenic agent is a cause of targeted somatic mutagenesis and of whether subjects with nucleic acid containing targeted somatic mutations has or will develop cancer based on a given mathematical model. An increased likelihood for example may be relative or absolute and may be expressed qualitatively or quantitatively. For instance, an increased likelihood or risk that a subject will develop cancer may be expressed as simply determining the number of targeted somatic mutations (as taught herein) and placing the test subject in an "increased likelihood or risk" category, based upon previous population studies.

In some embodiments, the methods comprise comparing the number or percentage of targeted somatic mutations to a preselected or threshold number or percentage. Thresholds may be selected that provide an acceptable ability to predict diagnosis, likelihood or prognostic risk. In illustrative examples, receiver operating characteristic (ROC) curves are calculated by plotting the value of a variable versus its relative frequency in two populations in which a first population has a first condition or risk and a second population has a second condition or risk (called arbitrarily, for example, "healthy condition" and "cancer", or "low risk" and "high risk").

A distribution of number of mutations for subjects with and without a disease will likely overlap. Under such conditions, a test does not absolutely distinguish a first condition and a second condition with 100% accuracy, and the area of overlap indicates where the test cannot distinguish the first condition and the second condition. A threshold is selected, above which the test is considered to be "positive" and below which the test is considered to be "negative." The area under the ROC curve (AUC) provides the C-statistic, which is a measure of the probability that the perceived measurement will allow correct identification of a condition (see, e.g., Hanley et al., Radiology 143: 29-36 (1982). The term "area under the curve" or "AUC" refers to the area under the curve of a receiver operating characteristic (ROC) curve, both of which are well known in the art. AUC measures are useful for comparing the accuracy of a classifier across the complete data range. Classifiers with a greater AUC have a greater capacity to classify unknowns correctly between two groups of interest (e.g., a healthy condition mutation status and a cancer mutation status). ROC curves are useful for plotting the performance of a particular feature in distinguishing or discriminating between two populations (e.g., cases having a cancer and controls without the cancer). Typically, the feature data across the entire population (e.g., the cases and controls) are sorted in ascending order based on the value of a single feature. Then, for each value for that feature, the true positive and false positive rates for the data are calculated. The sensitivity is determined by counting the number of cases above the value for that feature and then dividing by the total number of cases. The specificity is determined by counting the number of controls below the value for that feature and then dividing by the total number of controls. Although this definition refers to scenarios in which a feature is elevated in cases compared to controls, this definition also applies to scenarios in which a feature is lower in cases compared to the controls (in such a scenario, samples below the value for that feature would be counted). ROC curves can be generated for a single feature as well as for other single outputs, for example, a combination of two or more features can be mathematically combined (e.g., added, subtracted, multiplied, etc.) to produce a single value, and this single value can be plotted in a ROC curve. Additionally, any combination of multiple features (e.g., one or more other epigenetic markers), in which the combination derives a single output value, can be plotted in a ROC curve. These combinations of features may comprise a test. The ROC curve is the plot of the sensitivity of a test against the specificity of the test, where sensitivity is traditionally presented on the vertical axis and specificity is traditionally presented on the horizontal axis. Thus, "AUC ROC values" are equal to the probability that a classifier will rank a randomly chosen positive instance higher than a randomly chosen negative one. An AUC ROC value may be thought of as equivalent to the Mann-Whitney U test, which tests for the median difference between scores obtained in the two groups considered if the groups are of continuous data, or to the Wilcoxon test of ranks.

Alternatively, or in addition, thresholds may be established by obtaining an earlier mutation status result from the same patient, to which later results may be compared. In these embodiments, the individual in effect acts as their own "control group." In another embodiment, thresholds may be established by analysing the number targeted somatic mutations in nucleic acid from non-diseased or healthy tissue from a patient and comparing it to analysing the number targeted somatic mutations in nucleic acid from diseased or cancerous tissue.

The term "mutagenic agent" refers to an agent that can cause mutagenesis of DNA. Mutagenic agents include endogenous agents (i.e. agents that are endogenous to, or are produced by, the cell in which the DNA is contained) and exogenous agents (i.e. agents that are exogenous to, or not produced by, the cell in which the DNA is contained), and include for example chemicals, proteins, enzymes, radiation and viruses.

As used herein, a "mutation type" refers to the specific nucleotide substitution that comprises the mutation, and is selected from among C>T, C>A, C>G, G>T, G>A, G>C, A>T, A>C, A>G, T>A, T>C and T>G mutations. Thus, for example, a mutation type of C>T refers to a mutation in which the targeted or mutated nucleotide C is replaced with the substituting nucleotide T.

The "nucleic acid" as used herein designates DNA, cDNA, mRNA, RNA, rRNA or cRNA. The term typically refers to polynucleotides greater than 30 nucleotide residues in length.

The terms "patient" and "subject" are used interchangeably and refer to patients and subjects of human or other mammal and includes any individual it is desired to examine or treat using the methods of the invention. However, it will be understood that "patient" does not imply that symptoms are present. Suitable mammals that fall within the scope of the invention include, but are not restricted to, humans and other primates, livestock animals (e.g., sheep, cows, horses, donkeys, pigs), laboratory test animals (e.g., rabbits, mice, rats, guinea pigs, hamsters), companion animals (e.g., cats, dogs) and captive wild animals (e.g., foxes, deer, dingoes).

The term "somatic mutation" refers to a mutation in the DNA of somatic cells (i.e. not germ cells), occurring after conception. "Somatic mutagenesis" therefore refers to the process by which somatic mutations occur.

As used herein, "targeted somatic mutagenesis" refers to the process of somatic mutagenesis resulting from one or more mutagenic agents, wherein mutagenesis occurs at a targeted nucleotide within a motif, the targeted nucleotide is present at a particular position within a codon (e.g. the first, second or third, position of the mutated codon reading from 5' to 3', annotated MC-1, MC-2 and MC-3, respectively), and the targeted nucleotide is mutated to a particular substituting nucleotide (i.e. the mutation is of a particular mutation type, e.g. C>T, not C>A or C>G). Thus, a determination that targeted somatic mutagenesis is occurring requires analysis of the type of mutation (e.g. C>T), the motif at which the mutation occurs (e.g. WR<u>C</u>) and codon context of the mutation, i.e. the position within the codon at which the mutation occurs (e.g. MC-1, MC-2 or MC-3). "Targeted somatic mutagen" therefore refers to mutation resulting from targeted somatic mutagenesis.

As used herein, the terms "treatment," "treating," and the like, refer to obtaining a desired pharmacologic and/or physiologic effect. The effect may be prophylactic in terms of completely or partially preventing a condition (such as cancer) or symptom thereof and/or may be therapeutic in terms of a partial or complete cure for a condition and/or adverse affect attributable to the condition. "Treatment," as used herein, covers any treatment of condition in a mammal, particularly in a human, and includes: (a) preventing the condition from occurring in a subject which may be at risk of developing the condition but has not yet been diagnosed as having it; (b) inhibiting the condition, i.e., arresting its development; and (c) relieving the condition, i.e., causing regression of the condition.

As used herein, "whole exome" refers to all of the exons in the genome. Thus, analysis of the sequence of a whole exome from a cell refers to analysis of the sequence of all of the exons in the genome from the cell.

2. Mutagenic Agents Involved in Somatic Mutagenesis

Both exogenous and endogenous factors can act as mutagenic agents that cause or play a role in somatic mutagenesis. Exogenous factors include, but are not limited to, aflatoxins, 4-aminobiphenyl, aristolochic acids, arsenic compounds, asbestos, azathioprine, benzene, benzidine, beryllium and beryllium compounds, 1,3-butadiene, 1,4-butanediol dimethylsulfonate (busulfan, Myleran®), cadmium and cadmium compounds, chlorambucil, 1-(2-chloroethyl)-3-(4-methylcyclohexyl)-1-nitrosourea (MeCCNU), bis(chloromethyl)ether and technical-grade chloromethyl methyl ether, chromium hexavalent compounds, coal tar pitches, coal tars, coke oven emissions, cyclophosphamide, cyclosporin A, diethylstilbestrol (DES), erionite, ethylene oxide, formaldehyde, melphalan, methoxsalen with ultraviolet A therapy (PUVA), mustard gas, 2-naphthylamine, neutrons, nickel compounds, radon, crystalline silica (respirable size), solar radiation, soots, strong inorganic acid mists containing sulfuric acid, tamoxifen, 2,3,7,8-tetrachlorodibenzo-p-dioxin (TCDD), thiotepa, thorium dioxide, tobacco smoke, vinyl chloride, ultraviolet radiation, wood dust, X-radiation and gamma radiation. Endogenous factors include, but are not limited to, activation-induced cytidine deaminase (AID), apolipoprotein B mRNA-editing enzyme, catalytic polypeptide-like (APOBEC) cytidine deaminases, and error-prone DNA polymerases, such as DNA polymerase-eta.

2.1 AID

Activation-induced cytidine deaminase (AID) is an important enzyme in adaptive immunity, involved in somatic hypermutation (SHM) and class switch recombination of immunoglobulin genes in B cells. AID triggers SHM by deaminating cytidines to uracils (C>U) to diversify the immunoglobulin variable region genes (VDJ) and create new antigen-binding sites.

It has been well recognized that the mutation patterns resulting from these SHM processes that give rise to new antigen-binding sites are not random. Clustering and hotspots of mutational activity influenced by neighbouring base sequences have been identified, and the catalytic properties and specific mutation spectra resulting from AID and its involvement in AID-mediated DNA deamination of rearranged immunoglobulin variable region genes are well documented.

The SHM process is currently considered to occur in two phases. In phase 1, the gene encoding the AID protein is upregulated in germinal center B lymphocytes (Muramatsu et al. (2000) Cell 102: 553-563). AID then targets mutations to G:C base pairs at the reverse complement hotspots <u>G</u>YW/WR<u>C</u> (where Y=C/T, W=A/T, R=A/G; and the underlined nucleotides constitute the targeted base pair) by the direct deamination of cytidine to uracil (C>U) in the transcribed single stranded (ss) regions of the DNA exposed during transcription (Di Noia and Neuberger (2007) Annu Rev Biochem. 76: 1-22; Teng and Papavasiliou (2007) Annu Rev Genet 41:107-120). AID occupies the target cytidine before deamination (Bhutani et al. (2011) Cell 146: 866-872). The uracils in DNA are very mutagenic if left unrepaired and they activate a DNA base excision repair (BER) process involving uracil DNA glycosylase (UNG) causing apurinic apyrimidinic (AP), or 'abasic', sites, leading to ssDNA nicks (via an apurinic/apyrimidinic endonuclease activity, APE) and attracting further DNA patch repair activity (Peled et al. (2008) Ann Rev Immunol 26: 481-511). Once UNG triggers the BER pathways to remove the uracils, the abasic site created can, at replication and repair, be replaced by any of the bases A, G, C or T.

The main strand bias mutation pattern associated with phase 1 is characterized by dominant C>T and G>A transitions, and with the total number of mutations of G exceeding the number of C (Steele (2009) Mol Immunol 46: 305-320). It has been deduced that the resulting strand biased mutation pattern is consistent with the known mis-incorporation signature of mammalian RNA polymerase II copying the template DNA strand carrying AID lesions, uracils and AP sites (see e.g. Steele (2009) Mol Immunol 46: 305-320).

In phase 2, the mutations are targeted to A:T base pairs predominantly at W<u>A</u>-hotspot motifs and are distinctly strand-biased with mutations of A exceeding mutations of T by 2-3 fold (see e.g. Steele (2009) Mol Immunol 46: 305-320). In phase 2, G:U mispairs recruit the binding of the mismatch DNA repair heterodimer MSH2-MSH6 complex, which in turn recruits the error-prone Y family translesion protein DNA polymerase-eta targeting mutations in a short patch error-prone DNA repair process to both WA-sites and some other sequence stretches in the VDJ target sequence region.

Several studies suggest the possibility that aberrant AID-initiated SHM processes might result in the conversion of C>U in DNA outside of the germinal center environment, and thus contribute to oncogenesis in other genes (Beale et al. (2004) J Mol. Biol 337: 585-594; Marusawa H. (2008) Int J Biochem Cell Biol 40: 1399-1402). SHM-like activity has been found to occur in a range of genes such as BCL-6 in human tonsillar B cells (Yavuz et al. (2002) Mol Immunol 39: 485-493), the CD5/4, PIM 1 and CMYC genes in T-lymphomas (Kotani et al. (2005) PNAS 102: 4506-4511), and BCL-6 and C-MYC in B-lymphomas (Nilsen et al. (2005) Oncogene 24: 3063-3066). AID-initiated SHM activity has also been investigated as a potential source of TP53 mutations in a number of studies. In one such study, mutation targeting in TP53 in B-cell chronic lymphocytic leukaemia (B-CLL) was found to exhibit the characteristic traits of the SMH process (Malcikova et al. (2008) Molecular Immunology 45: 1525-9). Although the number of mutations was low for the two patients observed, the data reveal a significant bias to point mutations at CG pairs, and a significant preference for the RGYW/WRCY motifs (28% and 44% in the first and second patients, respectively). In the second patient, it was found that 6/8 point mutations affecting A:T pairs were localised at WA/TW motifs, which are a hallmark characteristic of the SHM single point mutation spectrum. A high expression of AID transcript was found in the first patient, but not in the second who was already IgVH-mutated. As shown herein and described in Lindley and Steele (ISRN Genomics (2013) 921418) and Lindley (Cancer Genet. (2013) 206(6):222-6), strand-biased SHM-like mutation processes appear closely associated with cancer.

There are also examples of infectious agents that actively induce AID expression and result in a TP53 mutation pattern that is consistent with the known characteristics of SHM activity in Ig genes. Examples include hepatitis C virus (Machida et al. (2004) Proc Natl Acad Sci U.S.A. 101: 4262-4267), Epstein Barr virus (Epeldegui et al. (2007) Mol. Immunol 44: 934-942) and *Helicobacter pylori* (Matsumoto et al. (2007) Nat Med. 13: 470-476). AID has been linked to B cell tumorogenesis and other cancers (Honjo et al. (2012) Adv Cancer Res. 2012; 113:1-44), and transgenic expression of AID causes tumor formation in mice (Okazaki et al. (2003) J Exp Med 197: 1173-1181).

2.2 APOBEC Cytidine Deaminases

In addition to AID, the human genome encodes several homologous APOBEC cytidine deaminases that are known to be involved in innate immunity and RNA editing (Smith et al. (2012) Semin. Cell. Dev. Biol. 23:258-268). In humans, at least APOBEC1, APOBEC3A, APOBEC3B, APOBEC3C, APOBEC3D, APOBEC3F, APOBEC3G and APOBEC3H are involved in providing innate immunity and/or cellular mRNA editing.

For example, APOBEC1 is responsible for ApoB pre-mRNA editing, where it causes deamination of cytidine 6666 to change a glutamine codon into a stop codon, thus generating a shorter form of ApoB (ApoB48). APOBEC1 can also deaminate cytidine in DNA (Harris et al. (2002) Mol Cell. 10:1247-1253; Petersen-Mahrt and Neuberger (2003) J Biol Chem. 278:19583-19586). The APOBEC3 enzymes deaminate mobile genetic elements (i.e. endogenous retroelements and exogenous viruses), mutating the DNA as a form of innate immunity. For example, APOBEC3G acts on HIV and other retroviruses (e.g. simian immunodeficiency virus (SIV), equine infectious anemia virus (EIAV), murine leukemia virus (MLV), and foamy virus (FV)) to mutate the minus-strand DNA during reverse transcription. Other APOBEC3 enzymes have also been shown to act on HIV and other retroviruses, as well as hepatitis B virus, parvovirus and AAV-2 (reviewed in Smith et al. (2012) Sem Cell Dev Biol 23:258-268).

Like AID, the APOBEC cytidine deaminases have been implicated in oncogenesis. For example, transgenic expression of APOBEC1 causes tumor formation in mice (Yamanaka et al. (1995) PNAS 92:8483-8487); high expression of APOBEC3B leads to somatic mutation in tumor-associated genes (Shinohara et al. (2012) Scientific Reports 2: 806); APOBEC3B is upregulated in at least breast, bladder, cervix (adenocarcinoma and squamous cell carcinoma), and head and neck cancer, with an associated increase in mutations at APOBEC3B motifs (Burns et al (2013) Nature 494: 366-370; Burns et al. (2013) Nature Genetics 45:977-983); and APOBEC enzyme mutation signatures have been shown to be widespread in a variety of cancers.

A study comparing targeting preferences for AID, APOBEC1 and APOBEC3G using a bacterial mutation assay demonstrated the critical importance of nucleotides immediately 5' and 3' of the targeted C for the specificities of the cytidine deaminases (Beale et al. (2004) J Mol. Biol 337: 585-594). While APOBEC3G can only deaminate cytidines on ssDNA, APOBEC1 can edit cytidines on DNA or dsRNAs. It was observed that 79% of transitions in the presence of APOBEC1 were associated with a 5' T, thus implying a motif of TG/CA for APOBEC1. The APOBEC3G motif is suggested as being CG/CG and/or CC (Beale et al. (2004) J Mol. Biol 337: 585-594; and Rathmore et al (2013). J. Mol. Biology 425(22):4442-54). Other studies indicate that other APOBEC enzymes, such as APOBEC3A, APOBEC3B and APOBEC3F have a TC motif, or a more stringent TCW motif (where W corresponds to either A or T) (Bishop et al. (2004) Curr Biol. 14:1392-1396; Thielen et al. (2010) J Biol Chem 285:27753-27766; Henry et al. (2009) PLoS One. 4:e4277; Shinohara et al. (2012) Scientific Reports 2: 806; Burns et al. (2013) Nature Genetics 45:977-983). APOBEC3H has been suggested to target a GA/TC motif.

3. Methods for Detecting Targeted Somatic Mutagenesis

As demonstrated herein, some mutagenic agents not only cause mutagenesis of a nucleotide at one or more particular motifs, but the motif and mutated nucleotide are recognized within the codon context, i.e. the mutated nucleotide is at a particular position within the codon structure, such as the first, second or third nucleotide in the mutated codon (read 5' to 3'). There is also a clear preference for the replacement or substituting nucleotide. This combination of motif-specific, and codon context-specific targeting by mutagenic agents is termed herein targeted somatic mutagenesis. By way of a non-limiting example, and as shown in FIG. 1, mutation of A at a WA motif in the non-transcribed strand of a nucleic acid molecule may preferentially occur at the first position of the mutated codon (MC-1) and be a mutation to C (i.e. A>C). Thus, the likelihood of whether or not targeted somatic mutation of a nucleic acid molecule has occurred can be determined by analysing the sequence of a nucleic acid molecule to determine the codon context of mutations of a mutation type (e.g. A>C) at one or more particular motifs (e.g. a WA motif). If there is no codon bias in the location of the mutations of the mutation type at the motif (i.e. the mutations are essentially evenly distributed across each position in the codons), then it is most likely that the mutations arose by chance and not as a result of targeted somatic mutagenesis by a mutagenic agent. However, if there is a higher than expected percentage or number of mutations of the mutation type at one particular position in codons (e.g. MC-1, MC-2 or MC-3 sites) in the nucleic acid molecule, then this indicates that targeted somatic mutagenesis has occurred or is likely to have occurred.

The "expected number or percentage" of the mutations described above is the number or percentage of mutations expected if the mutations are independent of other mutations and codon context, i.e. the distribution of mutations at each targeted nucleotide in each position in the codon is essentially even. Thus, for example, when assessing mutations arising across MC-1, MC-2 and MC-3 positions or sites, it would be expected that mutation of a nucleotide (e.g. A) to any one of the other three nucleotides (e.g. G, C or T) at any one of the three site (e.g. MC-1, MC-2 or MC-3) would occur as 1 in every 9 mutations (i.e. 1 in 3 chance of A to any one of G, C or T, and a 1 in 3 chance at any site, equaling a 1 in 9 chance overall) or approximately 11% of the time. When assessing mutations arising across just two of the nucleotide positions in the mutated codon, such as the MC-1 and MC-2 sites, it would be expected that mutation of a nucleotide (e.g. A) to any one of the other nucleotides (e.g. G, C or T) at either of the two sites (e.g. MC-1 or MC-2), would occur as 1 in every 6 mutations, or approximately 17% of the time (i.e. 1 in 3 chance of A to any one of G, C or T, and a 1 in 2 chance at any site, equaling a 1 in 6 chance overall). Similarly, when assessing mutations arising across just one of the sites (e.g. MC-1), it would be expected that mutation of a nucleotide (e.g. A) to any one of the other nucleotides (e.g. G, C or T) would occur as 1 in every 3 mutations, or approximately 33% of the time.

This is illustrated in FIG. 2, where the prevalence of C>T mutations at MC-1 sites (i.e. at the first nucleotide position within the mutated codon) is assessed to determine whether targeted somatic mutation has occurred or whether the observed mutations arise randomly. If mutation of cytosines across MC-1 and MC-2 sites at a WRC motif is random, then it would be expected that the type and position of the mutations is evenly distributed, and that a C>T mutation at MC-2 occurs once in every six times (or approximately 17%), with the other 5 mutations being C>A at MC-1, C>A at MC-2, C>G at MC-1, C>G at MC-2, and C>T at MC-1. In the particular example shown in FIG. 2, there are a total of 82 mutations of a cytosine at MC-1 or MC-2 sites at a WR C motif. If the mutagenesis was random, it would be expected that one sixth (or 17%) of these would be C>T mutations at MC-2 sites, equivalent to about 14 occurrences. However, in this example, there are 72 observed C>T mutations at MC-2 sites, indicating that targeted somatic mutagenesis of the nucleic acid has occurred.

Typically, when targeted somatic mutagenesis occurs as a result of the activity of one or more mutagenic agents and an assessment is made across the three sites of the codon (e.g. MC-1, MC-2 and MC-3), the particular mutations that are associated with the mutagenic agent are observed at least or about 20%, 25%, 30%, 35%, 40%, 45%, 50%, 55%, 60%, 65%, 70%, 75%, 80%, 85%, 90%, 95% or more of the time. When an assessment is made across at two sites (e.g. MC-1 and MC-2; MC-1 and MC-3; or MC-2 and MC-3), the particular mutations that are associated with the mutagenic agent are typically observed at least or about 30%, 35%, 40%, 45%, 50%, 55%, 60%, 65%, 70%, 75%, 80%, 85%, 90%, 95% or more of the time. When an assessment is made across only one site (e.g. MC-1; MC-2; or MC3), the particular mutations that are associated with the mutagenic agent are typically observed at least or about 50%, 55%, 60%, 65%, 70%, 75%, 80%, 85%, 90%, 95% or more of the time.

By assessing the type of mutation at a particular motif (e.g. C>T mutations at a WRC motif) as well as the codon context of the mutation (e.g. whether the mutation is at an MC-2 site), a more accurate assessment of the activity of the mutagenic agent can be made compared to when only the mutation at the motif is assessed and codon context is not factored in. Accordingly, using the methods described herein, the likelihood that a particular mutagenic agent or a mutagenic process, such as an AID-associated mutagenic process, is a cause of targeted somatic mutagenesis of a nucleic acid molecule can be assessed by analysing the sequence of the nucleic acid molecule to determine the codon context of mutations at motif(s) targeted by the mutagenic agent or mutagenic process.

3.1 Targeted Somatic Mutagenesis by AID, APOBEC1, APOBEC3G, APOBEC3H and Aflatoxin As described above, AID is known to target the motif GYW/WRC, wherein the underlined nucleotide is mutated. As demonstrated herein, there is a significant preference for targeting of the G to occur at MC-2 sites, resulting in G>A mutations. Accordingly, a higher than expected number or percentage of G>A mutations at GYW motifs at MC-2 sites in the non-transcribed strand of a nucleic acid molecule indicates that AID is a likely cause of targeted somatic mutagenesis of the nucleic acid, and that AID is active in the cells and/or tissue from which the nucleic acid was obtained. As also demonstrated herein, there is a significant preference for targeting of the C to occur at MC-1 sites, resulting in C>T mutations. Accordingly, a higher than expected number or percentage of C>T mutations at WRC motifs at MC-1 sites in the non-transcribed strand of a nucleic acid molecule indicates that AID is a likely cause of targeted somatic mutagenesis of the nucleic acid, and that AID is active in the cells and/or tissue from which the nucleic acid was obtained.

APOBEC3G is known to target CG/CG motifs. The studies described herein demonstrate that there is a significant preference for targeting of the G to occur at MC-2 sites, resulting in G>A mutations. Accordingly, a higher than expected number or percentage of G>A mutations at CG motifs at MC-2 sites in the non-transcribed strand of a nucleic acid molecule indicates that APOBEC3G is a likely cause of targeted somatic mutagenesis of the nucleic acid, and that APOBEC3G is active in the cells and/or tissue from which the nucleic acid was obtained. There is also a significant preference for targeting of the C to occur at MC-1 sites, resulting in C>T mutations. Accordingly, a higher than expected number or percentage of C>T mutations at CG motifs at MC-1 sites in the non-transcribed strand of a nucleic acid molecule indicates that APOBEC3G is a likely cause of targeted somatic mutagenesis of the nucleic acid, and that APOBEC3G is active in the cells and/or tissue from which the nucleic acid was obtained.

APOBEC3G is also known to target CC motifs. The studies described herein demonstrate that there is a significant preference for targeting of the C to occur at MC-1 sites, resulting in C>T mutations. Accordingly, a higher than expected number or percentage of C>T mutations at CC motifs at MC-1 sites in the non-transcribed strand of a nucleic acid molecule indicates that APOBEC3G is a likely cause of targeted somatic mutagenesis of the nucleic acid, and that APOBEC3G is active in the cells and/or tissue from which the nucleic acid was obtained.

APOBEC1 preferentially targets TG/CA motifs in nucleic acid molecules. Furthermore, there is a significant preference for targeting of the C at the CA motif to occur at MC-1 sites, resulting in C>T mutations. Accordingly, a higher than expected number or percentage of C>T mutations at CA motifs at MC-1 sites in the non-transcribed strand of a nucleic acid molecule indicates that APOBEC1 is a likely cause of targeted somatic mutagenesis of the nucleic acid, and that APOBEC1 is active in the cells and/or tissue from which the nucleic acid was obtained. There is also a preference for targeting of the G at the TG motif to occur at MC-2 sites, resulting in G>A mutations. Accordingly, a higher than expected number or percentage of G>A mutations at TG motifs at MC-2 sites in the non-transcribed strand of a nucleic acid molecule may indicate that APOBEC1 is a likely cause of targeted somatic mutagenesis of the nucleic acid, and that APOBEC1 is active in the cells and/or tissue from which the nucleic acid was obtained.

Somatic mutations at a WA motif are known to occur in phase 2 of the AID-associated SHM process in germinal center B cells, and are thus indicative of AID-associated mutations processes and, by extension, may be indicative of AID activity. As demonstrated herein, there is a preference for targeting of the A to occur at MC-2 sites, resulting in A>T mutations. Accordingly, a higher than expected number or percentage of A>T mutations at WA motifs at MC-2 sites in the non-transcribed strand of a nucleic acid molecule indicates that AID-associated somatic mutation processes are active in the cells and/or tissue from which the nucleic acid was obtained, and that AID may also be active in the cells and/or tissue. A determination that an AID-associated mutation process is a likely cause of targeted somatic mutagenesis can also made if the number or percentage of observed G>A mutations in GYW motifs at MC-2 sites, or C>T mutations in WRC motifs at MC-1 sites, which are representative of AID activity, can also be made.

Aflatoxin is associated with G>T transversions at the third position of codon 249 in TP53. It has been determined herein that there is a preference for targeting the G within a GG motif, wherein the targeted nucleotide is at a MC-3 site. Accordingly, a higher than expected number or percentage of G>T mutations at GG motifs at MC-3 sites in the non-transcribed strand of a nucleic acid molecule indicates that aflatoxin is a likely cause of targeted somatic mutagenesis of the nucleic acid. In particular examples, the aflatoxin is aflatoxin B1. In other examples, the aflatoxin is aflatoxin B2, G1, G2, M1 or M2.

3.2 Identifying Motifs for other Mutagenic Agents

As clearly demonstrated herein, mutagenic agents may target a nucleotide in a motif within a particular codon context. Thus, targeted somatic mutation by such agents generally results in one type of mutation (e.g. C>T, and not C>G or C>A), at one position within the codon structure (e.g. MC-1 and not MC-2 or MC-3) and at one motif (e.g. CG). By analysing nucleic acid sequences for the particular mutation type at the motif and within a particular codon context, as described above, a more accurate indication of the activity of a mutagenic agent can be obtained than if just the incidence of mutations at the motif were to be examined.

This bias for codon context can be used to identify motifs for other mutagenic agents. By analysing a nucleic acid molecule for the incidence of somatic mutations of a mutation type known to be associated with a mutagenic agent (e.g. G>T), and also assessing the codon context of the mutations and the nucleotides flanking the mutation, the motif for the mutagenic agent may be identified. When a particular mutation (e.g. G>T) occurs at a particular position within a codon (e.g. MC-3) more frequently than would occur at random, i.e. there is a preferred nucleotide position at which the mutation occurs, then it is likely that the mutations at this position occur as a result of targeted somatic mutation by the mutagenic agent. By analysing the nucleotides flanking the mutation at the preferred nucleotide position (e.g. MC-3), any motif common to the mutations and thus targeted by the mutagenic agent can be identified.

This is demonstrated in Example 7 below. A G>T transversion at the third position of codon 249 in TP53 has previously been linked to aflatoxin. When nucleic acid from a whole-exome sample from a subject with hepatocellular carcinoma was analysed for G>T mutations, it was observed that there were 9 G>T mutations at MC-3 sites, and each mutation was co-incident with another G immediately 5' of the mutated G, suggesting that aflatoxin targets GG motifs, wherein the targeted (underlined) G is at an MC-3 site, to cause G>T mutations.

Thus, the present invention also provides methods for identifying a motif targeted by a mutagenic agent. The methods involve analysing the sequence of a nucleic acid molecule to determine whether a mutation type associated with the mutagenic agent predominantly occurs at one position or site of a codon (e.g. MC-1, MC-2 or MC-3). If there is a co-incidence of mutation type and site, then the nucleotides flanking the mutated nucleotide are identified so as to identify a common motif that includes the mutated nucleotide. More specifically, the methods involve analysing the sequence of a nucleic acid molecule to identify somatic mutations of a mutation type known to be associated with the mutagenic agent, determining the codon context of the mutations to identify a preferred nucleotide position at which the mutations occur at a higher than expected frequency, and identifying the nucleotides flanking the mutations at the preferred nucleotide position so as to identify a motif that is common to the mutations.

A similar process can also be applied when the mutation type associated with a mutagenic agent is not yet known. In such cases, the sequence of a nucleic acid molecule is first analysed to identify somatic mutations, and any mutation type (e.g. G>T) that occurs at a position within a codon (e.g. MC-3) at a frequency that is higher than expected if the mutation occurred randomly (i.e. at a preferred nucleotide position) are also identified. The sequence flanking the mutation at the preferred nucleotide position is then assessed to determine whether there is a motif that is common to the mutation. If there is, this motif is likely the target of the mutagenic agent.

In other examples, known motifs of mutagenic agents can be further analysed to determine the codon bias and preference for a mutation type. Nucleic acid sequences can be assessed as described herein, such as in Example 1, to determine the codon context and mutation type associated with mutations at the motif so as to assess whether there is a preference for a mutation type at a nucleotide position in the codon. For example, APOBEC3A, APOBEC3B, APOBEC3F and APOBEC3H are thought to target a TC motif, or a more stringent TCW motif. The sequence of one or more nucleic acid molecules can be analysed to determine the codon context in which mutations at the motif occur, i.e. whether the C is at MC-1, MC-2 or MC-3, and what type of mutation occurs, (e.g. C>A, C>T, or C>G). Once the co-incident mutation type, motif and codon context are identified, this set of criteria, or diagnostic rule, can be used to more accurately determine whether APOBEC3A, APOBEC3B, APOBEC3F or APOBEC3H (or other mutagenic agent) is the likely cause of targeted somatic mutagenesis in a nucleic acid molecule and is thus active in the cells from which the nucleic acid was obtained.

To identify motifs and/or diagnostic rules using the methods described above, the nucleic acid that is analysed is typically nucleic acid that is known or suspected to have been in contact with the mutagenic agent or is nucleic acid that has been obtained from cells that are known or suspected to have been in contact with the mutagenic agent. For example, cells comprising the nucleic acid may be exposed in vitro to the mutagenic agent before nucleic acid is analysed. In other examples, the nucleic acid may be obtained from tissue or cells from subjects that are known to have been exposed to the mutagenic agent. Multiple studies using multiple samples may be performed to validate the findings.

3.3 Assessing the Nucleic Acid Molecule

Any method known in the art for obtaining and assessing the sequence of a nucleic acid molecule can be used in the methods of the present invention. The nucleic acid molecule analysed using the methods of the present invention can be any nucleic acid molecule, although is generally DNA (including cDNA). Typically, the nucleic acid is mammalian nucleic acid, such as human nucleic acid. The nucleic acid can be obtained from any biological sample. For example, the biological sample may comprise blood, tissue or cells. In some examples, the biological sample is a biopsy. Moreover, the sample may from any part of the body and may comprise any type of cells or tissue, such as, for example, breast, prostate, liver cells, colon, stomach, pancreatic, skin, thyroid, cervical, lymphoid, haematopoietic, bladder, lung, renal, rectal, ovarian, uterine, and head or neck tissue or cells, or cells from cerebrospinal fluid. In some instances, the nucleic acid is obtained from a cell or tissue sample from a subject suspected of or at risk of having cancer, or is obtained from a cell or tissue sample from a subject that has cancer.

The nucleic acid molecule can contain a part or all of one gene, or a part or all of two or more genes, and it is the sequence of this gene or genes that is analysed according to the methods of the invention. For example, the nucleic acid molecules may comprise all or part of the TP53, PIK3CA, ERBB2, DIRAS3, TET2 or nitric oxide synthase (NOS) genes. In some instances, the nucleic acid molecule comprises the whole genome or whole exome, and it is the sequence of the whole genome or whole exome that is analysed in the methods of the invention.

When using the methods of the present invention, the sequence of the nucleic acid molecule may have been predetermined. For example, the sequence may be stored in a database or other storage medium, and it is this sequence that is analysed according to the methods of the invention. In other instances, the sequence of the nucleic acid molecule must be first determined prior to employment of the methods of the invention. In particular examples, the nucleic acid molecule must also be first isolated from the biological sample.

Methods for obtaining nucleic acid and/or sequencing the nucleic acid are well known in the art, and any such method can be utilized for the methods described herein. In some instances, the methods include amplification of the isolated nucleic acid prior to sequencing, and suitable nucleic acid amplification techniques are well known to a person of ordinary skill in the art. Nucleic acid sequencing techniques are well known in the art and can be applied to single or multiple genes, or whole exomes or genomes. These techniques include, for example, capillary sequencing methods that rely upon 'Sanger sequencing' (Sanger et al. (1977) Proc Natl Acad Sci USA 74: 5463-5467) (i.e. methods that involve chain-termination sequencing), as well as "next generation sequencing" techniques that facilitate the sequencing of thousands to millions of molecules at once. Such methods include, but are not limited to, pyrosequencing, which makes use of luciferase to read out signals as individual nucleotides are added to DNA templates; "sequencing by synthesis" technology (Illumina), which uses reversible dye-terminator techniques that add a single nucleotide to the DNA template in each cycle; and SOLiD™ sequencing (Sequencing by Oligonucleotide Ligation and Detection; Life Technologies), which sequences by preferential ligation of fixed-length oligonucleotides. These next generation sequencing techniques are particularly useful for sequencing whole exomes and genomes.

Once the sequence of the nucleic acid molecule is obtained, single point somatic mutations are then identified. Single point mutations may be identified by comparing the sequence to a control sequence. The control sequence may be the sequence of a nucleic acid molecule obtained from a sample from a control individual, such as a healthy individual that is free of disease; the sequence of a nucleic acid molecule obtained from a control sample, such as a sample from healthy, non-diseased tissue; or may be a consensus sequence understood to contain no somatic mutations. In addition to identifying the single point mutations, the codon containing the mutation and the position of the mutation within the codon (MC-1, MC-2 or MC-3) is identified. Nucleotides in the flanking 5' and 3' codons are also identified so as to identify the motifs. Typically, for the methods of the present invention, the sequence of the non-transcribed strand (equivalent to the cDNA sequence) of the nucleic acid molecules is analysed). In some instances, the sequence of the transcribed strand is analysed.

FIG. 2 shows an example of the analysis that can be performed on nucleic acid from a biological sample as described above to determine whether APOBEC3G and/or AID are a likely cause of somatic mutagenesis. In this example, the location of single point mutations in the cDNA sequence (wherein the start codon "ATG" comprises the $1^{st}$, $2^{nd}$ and $3^{rd}$ nucleotides of the molecule) for sample PD3185a have been identified and their codon context determined so as to assess how many and what type of mutations at the GYW/WRC, CG/CG and WA motifs in each position occur. The data is then tabulated and statistical analyses applied to determine whether the mutations arose by chance or as a result of targeted somatic mutagenesis caused by AID and/or APOBEC3G. In this example shown in FIG. 2, because there are more G>A mutations in the GYW motif at MC-2 sites and more C>T mutations in the WRC motif at MC-1 sites on the non-transcribed strand than expected, it is likely that AID is a cause of targeted somatic mutagenesis in this nucleic acid molecule. Furthermore, because there are more G>A mutations in the CG motif at MC-2 sites on the non-transcribed strand than expected, it is likely that APOBEC3G is also a cause of targeted somatic mutagenesis in this nucleic acid molecule.

As demonstrated herein, using the methods of the present invention, only a small number of mutations at motifs need be analysed to determine with statistical significance whether targeted somatic mutagenesis has occurred as a result of the activity of particular mutagenic agent. In some instances, the number of mutations at a particular motif analysed using the methods of the present invention may be as few as 2 mutations. For example, if it is found that an apparently healthy patient has only 2 somatic mutations in the analysed nucleic acid, and both of these are G>A mutations in a GYW motif at an MC-2 site, then the probability that this pattern arose by chance is 0.04238 (p<95%, using a ChiSquare test, 9-1=9 df). Alternatively, the probability of each of the mutations occurring by chance can be said to be ⅑ (i.e. a ⅓ chance of a G>A mutation, and a ⅓ chance of the mutation being at an MC-2 sites, as discussed above), and the probability that 2 out of 2 mutations occur in this pattern is therefore ⅟₈₁ (or 0.012346). However, as would be understood by those skilled in the art, statistical significance may be improved when more mutations at a particular motif analysed. Thus, in some instances, the number of mutations at a particular motif analysed using the methods of the present invention may be at least 20. Many nucleic acid samples from subjects before or after treatment have 40 or more mutations, with some harbouring up to 400 or more mutations. Accordingly, the number of mutations at a particular motif analysed using the methods of the present invention may be at least or about 2, 3, 4, 5, 6, 7, 8, 9, 10, 15, 20, 25, 30, 40, 50, 60, 70, 80, 90, 100, 150, 200, 250, 300 or more.

All the essential materials and reagents required for detecting targeted somatic mutagenesis in a subject and further identifying the likelihood that a mutagenic agent is the cause of the targeted somatic mutagenesis, and related methods as described herein, may be assembled together in a kit. For example, when the methods of the present invention include first isolating and/or sequencing the nucleic acid to be analysed, kits comprising reagents to facilitate that isolation and/or sequencing are envisioned. Such reagents can include, for example, primers for amplification of DNA, polymerase, dNTPs (including labelled dNTPs), positive and negative controls, and buffers and solutions. Such kits also generally will comprise, in suitable means, distinct containers for each individual reagent. The kit can also feature various devices, and/or printed instructions for using the kit.

In some embodiments, the methods described generally herein are performed, at least in part, by a processing system, such as a suitably programmed computer system. A stand-alone computer, with the microprocessor executing applications software allowing the above-described methods to be performed, may be used. Alternatively, the methods can be performed, at least in part, by one or more processing systems operating as part of a distributed architecture. For example, a processing system can be used to identify mutation types, the codon context of a mutation and/or motifs within one or more nucleic acid sequences. In some examples, commands inputed to the processing system by a user assist the processing system in making these determinations.

In one example, a processing system includes at least one microprocessor, a memory, an input/output device, such as a keyboard and/or display, and an external interface, interconnected via a bus. The external interface can be utilised for connecting the processing system to peripheral devices, such as a communications network, database, or storage devices. The microprocessor can execute instructions in the form of applications software stored in the memory to allow the methods of the present invention to be performed, as well as to perform any other required processes, such as communicating with the computer systems. The applications software may include one or more software modules, and may be executed in a suitable execution environment, such as an operating system environment, or the like.

Figure 18:
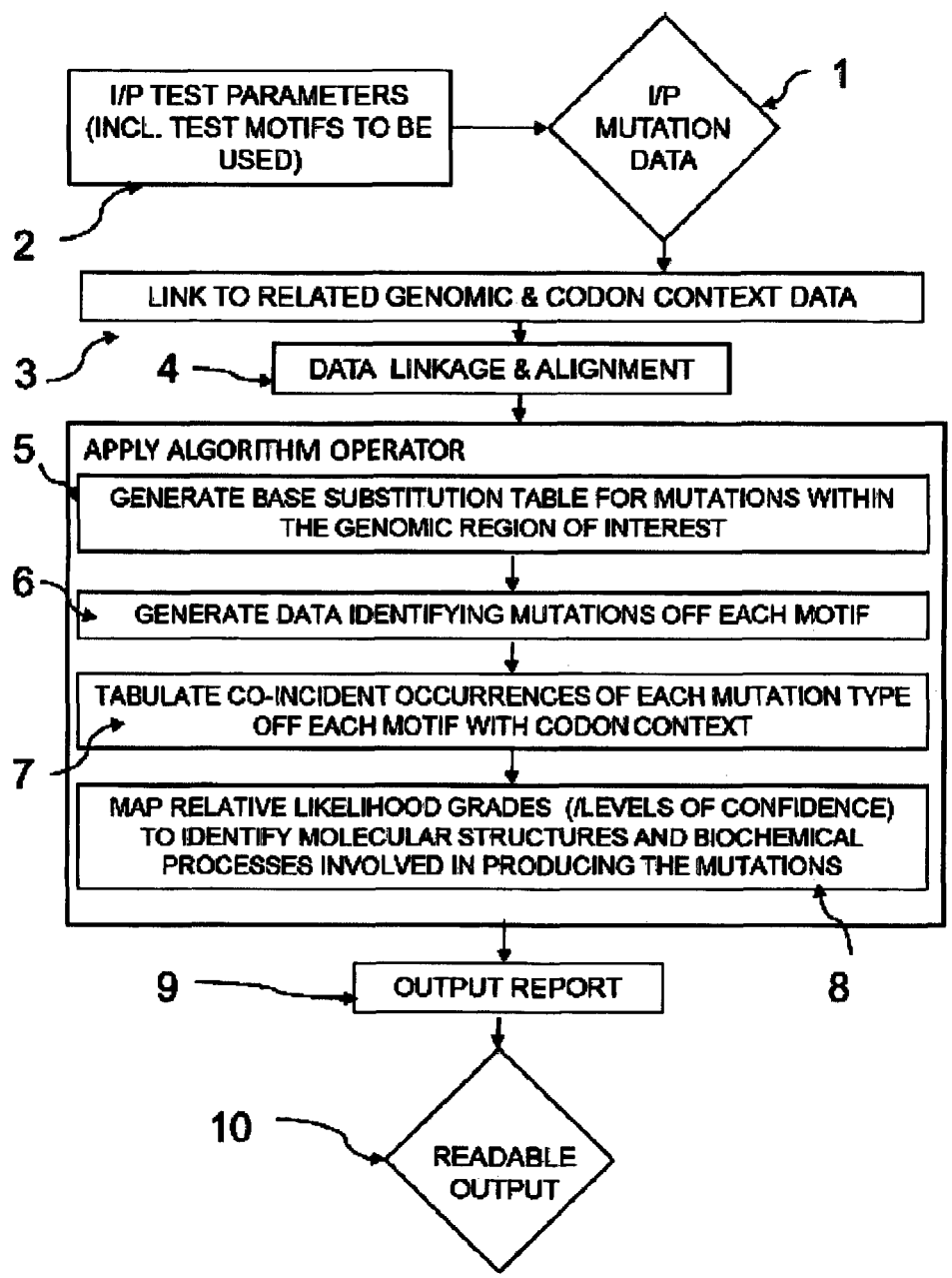
FIG. 18 is a schematic of the process of detecting targeted somatic mutagenesis in a nucleic acid molecule using a processing system.

In another example, the processing system can be used to upload sequence information and other relevant data from databases or other sources. Algorithms devised to be appropriate for the methods disclosed herein can be applied to data, such as shown in FIG. 18. In this example, input data [1] and test parameters (such as motifs to be used) [2] are uploaded or entered into the system. A base substitution table is then generated for mutations within the genomic region of interest with data aligned and linked to mutations with codon context data and other information linked to sample details and nucleotide sequence [3, 4, 5]. The next step involves the identification of co-incident occurrences of each mutation type at each motif at each nucleotide position within the codons [6]. The data are tabulated to record co-incident occurrences of each mutation type off each motif with codon context [7], including the relative likelihood grades with levels of confidence for each diagnosis [8]. The results are linked to identify the mutagenic agents (or molecular structures) and the biochemical processes likely to be involved in producing the mutations and relevant clinical information [8]. An output report is generated according to the service request information used as input [9] and a readable output is generated [10].

4. Diagnostic and Therapeutic Applications

The methods described herein for detecting whether targeted somatic mutation has occurred and determining the likelihood that a mutagenic agent is a cause of somatic mutagenesis of a nucleic acid molecule have many useful diagnostic and therapeutic applications. Somatic mutagenesis is known to be associated with the development and progression of many cancers. Similarly, some mutagenic agents are known to be associated with the development and progression of many cancers. Using the methods described herein, the presence and/or extent of targeted somatic mutagenesis resulting from one or more mutagenic agents, and the identity of the mutagenic agent that is the likely cause of somatic mutagenesis, can be determined. This can facilitate early diagnosis of cancer, a determination of the likelihood that a subject has or will develop cancer, and/or development of appropriate therapeutic or preventative protocols. In addition, ongoing assessment of targeted somatic mutations attributable to one or more mutagenic agents can be used to assess whether a cancer is progressing or regressing and/or the success or failure of a treatment regimen. For example, an increase in the number of targeted somatic mutations detected in nucleic acid from a sample, such as a biopsy, over time in the same subject can indicate a worsening of the cancer or a failure of a treatment regimen, while a stabilization or reduction in the number of mutations can indicate remission of the condition or success of a treatment regimen.

In particular instances, the methods of the present invention can extend to the diagnosis of cancer in a subject or a determination of the likelihood that a subject has or will develop cancer. For example, the likelihood that a subject has or will develop cancer can be assessed by analysing a nucleic acid molecule from a biological sample from the subject so as to determine whether targeted somatic mutagenesis by one or more mutagenic agents has occurred. If targeted somatic mutagenesis has occurred, a determination can be made that the subject is likely to have or to develop cancer.

In some examples, the diagnostic rules described above are utilized to determine the likelihood that targeted somatic mutagenesis has occurred. For example, targeted somatic mutagenesis can be detected when the number or percentage of observed G to A mutations in GYW motifs at MC-2 sites in the non-transcribed strand of the nucleic acid molecule is higher than expected; the number or percentage of observed C>T mutations in WRC motifs at MC-1 sites in the non-transcribed strand of the nucleic acid molecule is higher than expected; the number or percentage of observed G>A mutations in CG motifs at MC-2 sites in the non-transcribed strand of the nucleic acid molecule is higher than expected; the number or percentage of observed C>T mutations in CG motifs at MC-1 sites in the non-transcribed strand of the nucleic acid molecule is higher than expected; the number or percentage of observed C>T mutations in CA motifs at MC-1 sites in the non-transcribed strand of the nucleic acid molecule is higher than expected; the number or percentage of observed G>A mutations in GA motifs at MC-1 sites in the non-transcribed strand of the nucleic acid molecule is higher than expected; the number or percentage of observed G>A mutations in TG motifs at MC-2 sites in the non-transcribed strand of the nucleic acid molecule is higher than expected; the number or percentage of observed G>T mutations in GG motifs at MC-3 sites in the non-transcribed strand of the nucleic acid molecule is higher than expected; the number or percentage of observed C>T mutations in CC motifs at MC-1 sites in the non-transcribed strand of the nucleic acid molecule is higher than expected; or the number or percentage of observed A>G mutations in WA motifs at MC-2 sites in the non-transcribed strand of the nucleic acid molecule is higher than expected, as described above for AID, APOBEC3G, APOBEC3H, APOBEC1 and aflatoxin. In other examples, diagnostic rules determined for other mutagenic agents using the methods described herein are used to detect the occurrence of targeted somatic mutation.

In some instances, when targeted somatic mutations are detected in a sample containing cells or tissue from a particular region or location in a subject, such as breast, prostate, liver, colon, stomach, pancreatic, skin, thyroid, cervical, lymphoid, haematopoietic, bladder, lung, renal, rectal, ovarian, uterine, and head or neck tissue or cells, then a determination that the subject has or is likely to develop cancer involving that tissue or those cells is made. Thus, for example, a determination that the subject has or is likely to develop breast, prostate, liver, colon, stomach, pancreatic, skin, thyroid, cervical, lymphoid, haematopoietic, bladder, lung, renal, rectal, ovarian, uterine, or head and neck cancer may be made.

In particular examples, if it is observed that a mutagenic agent, such as AID or APOBEC3G, is the likely cause of targeted somatic mutagenesis of nucleic acid in prostate tissue or cells, then the subject may be diagnosed with prostate cancer or determined to be likely to have or to develop prostate cancer. Similarly, if it is observed that a mutagenic agent is the likely cause of targeted somatic mutagenesis of nucleic acid in breast tissue or cells, then the subject may be diagnosed with breast cancer or determined to be likely to have or to develop breast cancer.

The extent of targeted somatic mutagenesis by the mutagenic agent (i.e. the number of targeted somatic mutations attributable to the mutagenic agent in the nucleic acid) can also be used to assist in determining the likelihood that the subject has or will develop cancer, the cancer is progressing or regressing, and/or the treatment is working or not. Typically, the higher the number of targeted somatic mutagenesis, the higher the likelihood that the subject has or will develop cancer. Furthermore, if there is an increase in the number of targeted somatic mutations over time in a subject, the higher the likelihood that the cancer is progressing and/or the treatment has failed. Conversely, if there is a decrease in the number of targeted somatic mutations over time in a subject, the higher the likelihood that the cancer is regressing and/or the treatment has been successful.

The methods of the present invention also extend to therapeutic or preventative protocols. In instances where a subject is determined to be likely to develop cancer, protocols designed to reduce that likelihood may be designed and applied. For example, if a subject is determined to be at risk of developing a cancer associated with a particular mutagenic agent, the subject can be advised to reduce exposure to that mutagenic agent. For example, if a subject is determined to be at risk of developing melanoma, the subject can be advised to reduce exposure to UV radiation. In instances where a subject has been diagnosed with cancer or determined to have a high likelihood of developing cancer using the methods described above, an appropriate therapeutic protocol can be designed for the subject and administered. This may include, for example, radiotherapy, surgery, chemotherapy, hormone ablation therapy, pro-apoptosis therapy and/or immunotherapy. In some examples, further diagnostic tests may be performed to confirm the diagnosis prior to therapy.

Radiotherapies include radiation and waves that induce DNA damage for example, γ-irradiation, X-rays, UV irradiation, microwaves, electronic emissions, radioisotopes, and the like. Therapy may be achieved by irradiating the localized tumor site with the above described forms of radiations. It is most likely that all of these factors effect a broad range of damage DNA, on the precursors of DNA, the replication and repair of DNA, and the assembly and maintenance of chromosomes.

Dosage ranges for X-rays range from daily doses of 50 to 200 roentgens for prolonged periods of time (3 to 4 weeks), to single doses of 2000 to 6000 roentgens. Dosage ranges for radioisotopes vary widely, and depend on the half life of the isotope, the strength and type of radiation emitted, and the uptake by the neoplastic cells.

Non-limiting examples of radiotherapies include conformal external beam radiotherapy (50-100 Grey given as fractions over 4-8 weeks), either single shot or fractionated, high dose rate brachytherapy, permanent interstitial brachytherapy, systemic radio-isotopes (e.g., Strontium 89). In some embodiments the radiotherapy may be administered in combination with a radiosensitizing agent. Illustrative examples of radiosensitizing agents include but are not limited to efaproxiral, etanidazole, fluosol, misonidazole, nimorazole, temoporfin and tirapazamine.

Chemotherapeutic agents may be selected from any one or more of the following categories:

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulphan and nitrosoureas); antimetabolites (for example antifolates such as fluoropyridines like 5-fluorouracil and tegafur, raltitrexed, methotrexate, cytosine arabinoside and hydroxyurea; anti-tumor antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like paclitaxel and docetaxel; and topoisomerase inhibitors (for example epipodophyllotoxins like etoposide and teniposide, amsacrine, topotecan and camptothecin);

(ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), UH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab [Herceptin™] and the anti-erbb1 antibody cetuximab [C2251]), farnesyl transferase inhibitors, MEK inhibitors, tyrosine kinase inhibitors and serine/threonine kinase inhibitors, for example other inhibitors of the epidermal growth factor family (for example other EGFR family tyrosine kinase inhibitors such as N-(3-chloro-4-fluorophenyl)-7-methoxy-6-(3-morpholinopropoxy)quinazolin-4-amine (gefitinib, AZD1839), N-(3-ethynylphenyl)-6,7-bis (2-methoxyethoxy)quinazolin-4-amine (erlotinib, OSI-774) and 6-acrylamido-N-(3-chloro-4-fluorophenyl)-7-(3-morpholinopropoxy)quinazoli-n-4-amine (CI 1033)), for example inhibitors of the platelet-derived growth factor family and for example inhibitors of the hepatocyte growth factor family;

(v) anti-angiogenic agents such as those which inhibit the effects of vascular endothelial growth factor, (for example the anti-vascular endothelial cell growth factor antibody bevacizumab [Avastin™], compounds such as those disclosed in International Patent Applications WO 97/22596, WO 97/30035, WO 97/32856 and WO 98/13354) and compounds that work by other mechanisms (for example linomide, inhibitors of integrin αvβ3 function and angiostatin);

(vi) vascular damaging agents such as Combretastatin A4 and compounds disclosed in International Patent Applications WO 99/02166, WO00/40529, WO 00/41669, WO01/92224, WO02/04434 and WO02/08213;

(vii) antisense therapies, for example those which are directed to the targets listed above, such as ISIS 2503, an anti-ras antisense; and (viii) gene therapy approaches, including for example approaches to replace aberrant genes such as aberrant p53 or aberrant GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy.

Immunotherapy approaches, include for example ex-vivo and in-vivo approaches to increase the immunogenicity of patient tumor cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumor cell lines and approaches using anti-idiotypic antibodies. These approaches generally rely on the use of immune effector cells and molecules to target and destroy cancer cells. The immune effector may be, for example, an antibody specific for some marker on the surface of a malignant cell. The antibody alone may serve as an effector of therapy or it may recruit other cells to actually facilitate cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a malignant cell target. Various effector cells include cytotoxic T cells and NK cells.

Examples of other cancer therapies include phototherapy, cryotherapy, toxin therapy or pro-apoptosis therapy. One of skill in the art would know that this list is not exhaustive of the types of treatment modalities available for cancer and other hyperplastic lesions.

In some instances, where the likely identity of the mutagenic agent causing the targeted somatic mutations is determined, therapy or preventative measures may include administration to the subject of an inhibitor of that mutagenic agent. Inhibitors can include, for example, siRNAs, miRNAs, protein antagonists (e.g. dominant negative mutants of the mutagenic agent), small molecule inhibitors, antibodies and fragments thereof. For example, commercially available siRNAs and antibodies specific for APOBEC cytidine deaminases and AID are widely available and known to those skilled in the art. Other examples of APOBEC3G inhibitors include the small molecules described by Li et al. (ACS Chem Biol. (2012) 7(3): 506-517), many of which contain catechol moieties, which are known to be sulfhydryl reactive following oxidation to the orthoquinone. APOBEC1 inhibitors also include, but are not limited to, dominant negative mutant APOBEC1 polypeptides, such as the mul (H61K/C93S/C96S) mutant (Oka et al. (1997) J Biol Chem 272, 1456-1460).

Typically, therapeutic agents will be administered in pharmaceutical compositions together with a pharmaceutically acceptable carrier and in an effective amount to achieve their intended purpose. The dose of active compounds administered to a subject should be sufficient to achieve a beneficial response in the subject over time such as a reduction in, or relief from, the symptoms of cancer, and/or the reduction, regression or elimination of tumours or cancer cells. The quantity of the pharmaceutically active compounds(s) to be administered may depend on the subject to be treated inclusive of the age, sex, weight and general health condition thereof. In this regard, precise amounts of the active compound(s) for administration will depend on the judgment of the practitioner, and those of skill in the art may readily determine suitable dosages of the therapeutic agents and suitable treatment regimens without undue experimentation.

In order that the invention may be readily understood and put into practical effect, particular preferred embodiments will now be described by way of the following non-limiting examples.

EXAMPLES

Example 1

Analysis of TP53 Somatic Mutations in Breast Cancer

The frequency and context of somatic mutations in the TP53 gene in breast cancers was assessed by accessing the IARC TP53 database and extracting data specific for breast cancer. The number of point mutations in this dataset was large (N=2,514). Most of the mutations were single point mutations, predominantly focused in the DNA binding region (codons ~130-300) of TP53. Only a minor fraction of the samples carried an exonic mutation in TP53. It was assumed that there are only slight variations due to base composition of TP53, and no corrections were made. Selection of various criteria facilitated construction and analysis of all types of mutations with 5' and 3' flanking sequence context in relation to the unmutated TP53 exon sequence (and in some cases intronic sequence). This facilitated the development of frequency distributions of various types of mutation (e.g., A-to-G) versus nucleotide and codon position across regions of interest.

The sequences of the cDNA transcripts (i.e. the same sequence context as the non-transcribed strands) were analysed. cDNA transcripts were used as these are publicly available in the COSMIC and Ensembl databases for extraction and analysis purposes. Using these transcripts, the sequence context around each mutation was analysed for mutations at the AID motif (GYW/WRC), APOBEC1 motif (TG/CA) and APOBEC3G motif (CG/CG), as well as the W A motif, which is representative of potential sites for mutations at A:T base pairs in phase II of the SHM process (and thus associated with AID activity). The mutations were assessed in relation to their positions in a mutated codon FIG. 1 shows an example of a mutated sequence in the defined 'region of interest' for this analysis. The region of interest includes 9 nucleotides encompassing the mutated codon, the flanking 5-prime (5') codon and the 3-prime (3') codon. The respective positions of the nucleotides in the mutated codon (MC) sequence are annotated as MC-1, MC-2 and MC-3 (read 5' to 3'). The respective positions of the nucleotides (N) in the flanking 5' codon are annotated as 5'N1. 5'N2 and 5'N3 respectively (also read 5' to 3'). Similarly, the positions of the nucleotides in the flanking 3'-codon are annotated as 3'N1, 3'N2 and 3'N3 respectively. In the example shown for an A-to-C point mutation (A>C), an A at an MC-1 site on the non-transcribed strand (NTS) is mutated to a C in the replicated non-transcribed strand (NTS'). The mutation of A in the mutated codon is associated with a G in the 5'-N3 position. This is annotated as "S . . . A" (where S is a G or C). This annotation is used regardless of the location of a mutation within the mutated codon.

The codon context and frequency of each of the 2,514 somatic mutations in the TP53 gene from the pooled breast cancer dataset is shown in Table 1. As noted above, MC-1, MC-2 and MC-3 refer to the position of the mutations within the mutated codon (MC). These are read 5' to 3' from the non-transcribed strand. To determine whether codon context was important for each mutation type, a Chi square test was used to test statistical significance against a cut-off at the $P<0.01$ level (2 DF).

TABLE 1

| Mutation | Location of all mutations within mutated codon | | | |
|---|---|---|---|---|
|  | MC-1 (p, 2df) | MC-2 (p, 2df) | MC-3 (p, 2df) | Total |
| A > T | 30 | 29 | 0 (p < 0.001) | 59 |
| A > C | 11 | 30 (p < 0.001) | 2 (p < 0.01) | 43 |
| A > G | 64 | 194 (p < 0.001) | 11 (p < 0.001) | 269 |
| Total off A | 105 | 253 | 13 | 371 |
| T > A | 30 | 29 | 8 | 67 |
| T > C | 48 | 64 (p < 0.01) | 18 (p < 0.001) | 130 |
| T > G | 23 | 44 | 19 | 86 |
| Total off T | 101 | 137 | 45 | 283 |
| C > A | 23 | 22 | 23 | 68 |
| C > T | 397 (p < 0.001) | 118 (p < 0.001) | 78 (p < 0.001) | 593 |
| C > G | 42 | 25 | 22 | 89 |
| Total off C | 462 | 165 | 123 | 750 |
| G > A | 203 (p < 0.001) | 505 (p < 0.001) | 87 (p < 0.001) | 795 |
| G > T | 69 | 87 | 37 (p < 0.01) | 193 |
| G > C | 35 | 67 (p < 0.001) | 20 (p < 0.01) | 122 |
| Total off G | 307 | 659 | 144 | 1110 |
| Total | 975 | 1214 | 325 | 2514 |

It was observed that there were far more transitions (i.e. A<>G or C<>T) than transversions (i.e. A or G<>C or T). As a result, the mutation pattern shows significant strand biases where mutations of A exceed mutations of T (371/283=1.3), and mutations of G exceed mutations of C (1110/750=1.5). This is in agreement with previous work showing similar strand bias patterns for SHM processes in VDJ regions of Ig genes, as well as protein kinase gene mutation data across the whole genome for a range of non-lymphoid cancers that include breast cancer (Steele and Lindley (2010) DNA Repair 9: 600-603). The strand bias pattern is also in agreement with mutation data taken from B-cell chronic lymphocytic leukaemia patients (Malcikova et al. (2008) Molecular Immunology 45: 1525-9).

The pooled dataset shown in Table 1 also revealed significant mutation codon bias patterns not previously reported. The most significant codon context biases were for transitions C>T (P<0.001, 2DF), G>A (P<0.001, 2DF) and A>G (P<0.001, 2DF), which are known to result in the hallmark strand bias patterns associated with SHM processes.

It was found that 397/593 (66.9%) of all C>T transitions occurred at an MC-1 site, and 397/750 (52.9%) of all mutations of C (i.e. C>A/G/T) were C>T transitions at an MC-1 site. In contrast, 505/795 (63.5%) of all G>A transitions occurred at an MC-2 site, and 505/1110 (45.5%) of all mutations of G (i.e. G>A/C/T) were G>A transitions at an MC-2 site. If mutations occur randomly and independently of the codon structure, it is expected that only 1 in 9 (or around 11.1%) of mutations would occur at a particular site (i.e. MC-1, MC-2 or MC-3) for each of the 3 different types of mutation of a particular nucleotide.

For the A>G transitions, 194/269 (72.1%) of all A>G transitions occurred at an MC-2 site, and 194/371 (52.3%) of all mutations of A (i.e. A>C/G/T) were A>G transitions at an MC-2 site.

The data in Table 1 also support the expectation of selection for missensed mutations in the TP53 gene as the number of mutations in the MC-3 were significantly less than in the MC-1 or MC-2 positions for each of the transitions C>T, G>A and A>G. For RNA, the nonsense-mediated mRNA decay (NMD) pathway is one known cellular surveillance system that relies on, codon context information to enable the cell to identify and dispose of defective gene products containing 'nonsense' mutations or STOP signals (UAG, UGA and UAA) that might prematurely stop translation. The result is selection for missense mutations in TP53. The data is also consistent with another previous study that reported a trend for higher than expected mutability for codon positions MC-1 and MC-2 in complementary-determining regions of Ig variable (V) region genes (Shapiro et al. (2002) J. Immunology 168: 2302-2306).

The analysis also revealed a highly significant statistical preference for C>T transitions to occur at MC-1 sites (P<0.001, 2DF), and for G>A transitions to occur at MC-2 sites (P<0.001, 2DF). As cytidines on the TS or the NTS of ssDNA in an open "transcription bubble" are both able to undergo deamination, the data support the conclusion that the molecular mechanisms involved are able to read in-frame, and distinguish between cytidines on the TS and the NTS.

Table 2 shows the codon context of the 2514 somatic mutations for the TP53 breast cancer dataset occurring at AID, APOBEC1 and APOBEC3G motifs, as well as WA motifs. A CM square test was used to determine statistical significance against a cut-off at the P<0.01 level (2 DF).

If mutations occur independently of the 5'-codon structure, and no correction is made for base composition, then it is expected that around one third of each mutation type will be located at an MC-1, MC-2 or MC-3 site. Similarly, it is expected that only around one ninth (11.1%) of all mutations of a single nucleotide will be located at an MC-1, MC-2 or MC-3 site. It was found that the codon context bias for transitions at key motifs associated with AID, APOBEC1 and APOBEC3G activity was even more statistically significant than what was found in the pooled dataset shown in Table 1.

TABLE 2

| Mutation | MC-1 (p, 2df) | | MC-2 (p, 2df) | | MC-3 (p, 2df) | | Total |
|---|---|---|---|---|---|---|---|
| GYW/WRC sites (AID) | | | | | | | |
| G > A | 9 | (p < 0.0001) | 185 | (p < 0.0001) | 6 | (p < 0.0001) | 200 |
| G > T | 3 | | 32 | (p < 0.0001) | 2 | | 37 |
| G > C | 0 | | 10 | | 1 | | 11 |
| C > A | 7 | | 9 | | 0 | | 16 |
| C > T | 106 | (p < 0.0001) | 13 | (p < 0.0001) | 13 | (p < 0.0001) | 132 |
| C > G | 3 | | 2 | | 15 | (p < 0.01) | 20 |
| CG/CG sites (APOBEC3G) | | | | | | | |
| G > A | 46 | (p < 0.0001) | 358 | (p < 0.0001) | 3 | (p < 0.0001) | 407 |
| G > T | 19 | | 24 | | 2 | (p < 0.01) | 45 |
| G > C | 10 | | 43 | (p < 0.0001) | 0 | (p < 0.0001) | 53 |
| C > A | 6 | | 0 | | 7 | | 13 |
| C > T | 240 | (p < 0.0001) | 6 | (p < 0.0001) | 2 | (p < 0.0001) | 248 |
| C > G | 20 | (p < 0.01) | 1 | | 6 | | 27 |
| TG/CA sites (APOBEC1) | | | | | | | |
| G > A | 46 | | 62 | | 47 | | 155 |
| G > T | 17 | | 38 | (p < 0.01) | 9 | | 64 |
| G > C | 7 | | 4 | | 6 | | 17 |
| C > A | 6 | | 2 | | 6 | | 14 |
| C > T | 93 | (p < 0.0001) | 16 | (p < 0.0001) | 51 | | 160 |
| C > G | 5 | | 5 | | 4 | | 14 |
| WA sites | | | | | | | |
| A > T | 5 | | 5 | | 0 | | 10 |
| A > C | 0 | | 15 | (p < 0.0001) | 1 | (p < 0.01) | 16 |
| A > G | 7 | (p < 0.0001) | 128 | (p < 0.0001) | 6 | (p < 0.0001) | 141 |

For GYW motifs linked to AID activity, 185/200 (92.5%) of all G>A transitions occurred at an MC-2 site, and 185/248 (74.6%) of all mutations at GYW sites (i.e. G>A/C/T) were G>A transitions at an MC-2 site. In contrast, at WRC sites, 106/132 (80.3%) of all C>T transitions occurred at an MC-1 site, and 106/168 (63.1%) of all mutations of C (i.e. C>A/G/T) were C>T transitions at an MC-1 site.

At CG motifs linked to APOBEC3G activity, 358/407 (87.7%) of all G>A transitions occurred at an MC-2 site, and 358/505 (70.9%) of all mutations at CG sites (i.e. G>A/C/T) were G-to-A transitions at an MC-2 site. In contrast, at CG sites, 240/248 (96.8%) of all C>T transitions occurred at an MC-1 site, and 240/288 (83.3%) of all mutations of C (i.e. C>A/G/T) were C>T transitions at an MC-1 site.

For the TG/CA motifs linked to APOBEC1 activity, the codon context bias was not as statistically significant. At CA sites, 93/160 (58.1%) of C>T transitions occurred at an MC-1 site, and 93/188 (49.5%) of all mutations of C (i.e. C>A/G/T) were C>T transitions at an MC-1 site. Only 62/155 (40.0%) of all G>A transitions at a TG site occurred at an MC-2 site, and 62/136 (45.6%) of all mutations of G (i.e. G>A/C/T) at TG sites were G>A transitions at an MC-2 site.

Another feature of the observed codon bias patterns at the key motifs shown in Table 2 is that the majority of all mutations of G for each at the motifs for AID, APOBEC1 and APOBEC3G preferentially occur at an MC-2 site. By comparison, most of the mutations of C for each of the motifs occurred at an MC-1 target site. This implies that an in-frame sensing mechanism is involved at the level of DNA during the initiation of transcription, and that it is able to distinguish between cytidines on the NTS and those on the TS in the context of an open "transcription bubble".

For the A>G transitions at WA sites, 128/141 (90.8%) occurred at an MC-2 site, and 128/167 (76.6%) of all mutations of A at WA sites (i.e. A>C/G/T) were G>A transitions at an MC-2 site. As an elevated level of A>G mutations at WA sites are recognised as a characteristic feature of SHM activity and diagnostic of the involvement of an RNA template intermediate, this finding supports a prediction that endogenous AID-initiated mutation processes are active in at least many of the samples in the dataset.

Table 3 shows the codon context of mutations occurring at key motifs associated with AID, APOBEC1 and APOBEC3G and co-located with a strong nucleotide (S=G/C) in the 5'N3 position. The annotation 'S . . . M' (where M is the mutated nucleotide A, G, C or T) is used to indicate the presence of an 'S' nucleotide in the 5'N3 position flanking the mutated codon, and with the mutated nucleotide target in any one of the positions MC-1, MC-2 or MC-3. If mutations occur independently of the 5'-codon structure, and no correction is made for base composition, then it is expected that only half of the mutations at each of the motifs will be co-located with an S in the 5'N3 position.

TABLE 2

| Mutation | MC-1 | MC-2 | MC-3 |
|---|---|---|---|
| Mutations at GYW/WRC (AID) AND S .. G/C sites | | | |
| G > A | 2/9 | 184/185 (99.5%) | 4/6 |
| G > T | 2/3 | 31/32 | 2/2 |
| G > C | 0/0 | 10/10 | 1/1 |
| C > A | 5/7 | 0/9* | 0/0 |
| C > T | 102/106 (96.2%) | 0/13* | 9/13 |
| C > G | 3/3 | 0/2* | 8/15 |
| Mutations at CG/CG (APOBEC3G) AND S .. G/C sites | | | |
| G > A | 46/46* | 352/358 (98.3%) | 2/3 |
| G > T | 19/19* | 24/24 | 2/2 |
| G > C | 10/10* | 41/43 | 0/0 |
| C > A | 6/6 | 0/0 | 7/7 |
| C > T | 239/240 (99.6%) | 6/6 | 2/2 |
| C > G | 20/20 | 1/1 | 4/6 |
| Mutations at TG/CA (APOBEC1) AND S .. G/C sites | | | |
| G > A | 0/46* | 36/62 (58.1%) | 34/47 |
| G > T | 0/17* | 27/38 | 9/9 |
| G > C | 0/7* | 3/4 | 5/6 |
| C > A | 4/6 | 2/2 | 4/6 |
| C > T | 52/93 (55.9%) | 10/16 | 45/51 |
| C > G | 5/5 | 5/5 | 2/4 |
| Mutations at WA AND S .. A sites | | | |
| A > T | 0/5* | 4/5 | 0/0 |
| A > C | 0/0* | 11/15 | 0/1 |
| A > G | 0/8* | 121/127 (95.3%) | 6/6 |

*It is impossible for a nucleotide in the 5'N3 position to be both 'S' and WA or TG for mutations at the MC-1 position. Similarly, the nucleotides in the 5'N3 position cannot be 'S' and WRC for mutations at the MC-2 position, and all mutations at a CG site at the MC-1 position have an 'S' in the 5'N3 position.

The analysis revealed an unexpectedly high linkage between S . . . M sites and transitions at motifs associated with AID, APOBEC3G activity and at WA sites, but not APOBEC1 sites. For the GYW/WRC motifs associated with AID activity, 184/185 (99.5%) of all G>A transitions in the MC-2 position had an S present in the 5'N3 position, and 102/106 (96.2%) of all C>T transitions in the MC-1 position had an S present in the 5'N3 position. For the CG/CG motifs associated with APOBEC3G activity, 352/358 (98.3%) of all G>A transitions in the MC-2 position had an S present in the 5'N3 position, and 239/240 (99.6%) of all C-to-T transitions in the MC-1 position had an S present in the 5'N3 position. For the TG/CA motifs associated with APOBEC1 activity, the results were not statistically significant. Only 36/62 (58.1%) of G>A transitions at an MC-2 site had an S present in the 5'N3' position, and 52/93 (55.9%) of C-to-T transitions in the MC-1 position had an S present in the 5'N3 position. For WA sites, 121/127 (95.3%) of A-to-G transitions at an MC-2 site had an S present in the 5'N3 position.

The data in Table 3 also reveal an unexpectedly high proportion of some of the transversions at the selected motifs being co-located with an S in the 5'N3 position. In particular, there is a higher than expected linkage between G-to-T/C mutations at GYW or CG target sites and an S . . . G site. For all transitions and transversions of G occurring at an MC-2 target for the selected AID, APOBEC3G and WA motifs, a highly significant 778/799 (97.4%) are co-located with an S . . . G. Similarly, 375/382 (98.2%) of all transitions and transversions of C occurring at an MC-1 target site for the selected AID and APOBEC3G motifs, are co-located with an S . . . C.

The co-location of an S . . . M (M=A/G/C/T) therefore appears to be an integral part of the direct contact binding and codon reading frame sensor mechanisms associated with AID and APOBEC3G deaminase activity, as well as the mutator mechanism(s) acting on WA sites.

Example 2

Development of Diagnostic Rules to Predict the Activity of AID, APOBEC1 or APOBEC3G The codon bias patterns observed for mutation at the AID, APOBEC1, APOBEC3G and WA motifs (described above) were used to generate the following "rules" or diagnostic criteria for use in predicting whether targeted somatic mutation (TSM) of a nucleic acid molecule is occurring as a result of AID, APOBEC1 and/or APOBEC3G activity:

A higher than expected number of G>A mutations off the GYW (AID) motif at MC-2 sites is associated with AID deaminase activity on the transcribed strand.

A higher than expected number of C>T mutations off the WRC (AID) motif at MC-1 sites is associated with AID deaminase activity on the non-transcribed strand.

A higher than expected number of G>A mutations off the CG (APOBEC3G) motif at MC-2 sites is associated with APOBEC3G activity.

A higher than expected number of C>T mutations off the CG (APOBEC3G) motif at MC-1 sites is associated with APOBEC3G activity.

A higher than expected number of A>G mutations off the WA motif at MC-2 is an indication of AID-linked mutation processes and thus AID activity.

When applying these rules, it is assumed that the set of mutations off each nucleotide are independent of each other, and that if the mutagenic agents are not present, the distribution of mutations off each nucleotide in each of the codon sites MC-1 and MC-2 will be randomly distributed for mutations off A, G, C or T.

FIG. 2 shows an example of how the above diagnostic criteria can be used to determine the probability that the codon-bias mutation distribution arose by chance or by targeted somatic mutation by AID or APOBEC3G. For each of the above selected diagnostic categories, the number of Observed (O) and the Expected (E) mutations are tabulated in Table form. For each of the diagnostic categories, the number of Expected (E) mutations is calculated using the total number of mutations likely to arise across MC-1 and MC-2 sites for each of the 3 possible types of mutation off a particular nucleotide if the mutations are random. (When analyzing mutations of the TP53 gene, as shown in FIG. 2, mutations occurring at MC-3 sites were excluded as a comparator as mutated variants of the TP53 gene have been selected for binding function. The nonsense-mediated messenger RNA decay (NMCD) pathway involved is one known cellular surveillance system that relies on codon context information to enable the cell to identify and dispose of defective gene products containing nonsense mutations or STOP signals that might prematurely stop translation). For example, in regards to the WR<u>C</u> motif that is associated with AID activity resulting in mutations of cytosine (C) off the non-transcribed strand, if the number of mutations at C were randomly distributed, the mutations would be evenly distributed across the MC-1/MC-2 sites and across C>A, C>G and C>T (C>A/G/T). Thus, in this example the Expected (E) number of C>T mutations at an MC-1 site is the total number of observed C>A/T/G mutations at MC-1 and MC-2 sites (i.e. 1+1+72+6+1+1), divided by the number of possible types/positions of mutations (i.e. 6), which equals 13.67. A simple CHISQUARE test is then applied to determine the probability that the observed distribution arose by chance. In the example shown in FIG. 3, the probability that the MC-1/MC-2 codon-bias distribution arose by chance for the selected set of diagnostic criteria applied to the mutation set for the TET2 gene is 7.42E-128. This result implies a very high level of significance (P<1E-127).

Referring again to FIG. 3, the higher than expected number of G>A mutations off the <u>G</u>YW motif at MC-2 sites and higher than expected number of C>T mutations off the WR<u>C</u> motif at MC-1 sites indicates AID deaminase activity, while the higher than expected number of G>A mutations off the CG motif at MC-2 sites and higher than expected number of C>T mutations off the <u>C</u>G motif at MC-1 sites indicates APOBEC3G activity.

Example 3

Analysis of TP53 Somatic Mutations in Other Cancers

To determine whether the codon bias for mutations at the AID, APOBEC3G and W<u>A</u> motifs observed in TP53 in breast cancer samples also occurs in TP53 in other cancers, data was extracted from the IARC TP53 database for cervical cancer (all types), cervical adenocarcinoma, colon adenocarcinoma, hepatocellular carcinoma, pancreatic cancer, prostate cancer, and malignant melanoma and analysed as described above.

FIGS. 4-11 show the frequency and location within codons of mutations at <u>G</u>YW/WR<u>C</u> sites (AID), C<u>G</u>/<u>C</u>G sites (APOBEC3G) and W<u>A</u> sites. As shown in these figures, the codon bias patterns for mutations at the AID, APOBEC3G and/or W<u>A</u> motifs in TP53 were observed in each of these cancers, indicating that there is a statistically very high likelihood that a wide range cancers with TP53 mutations are associated with AID/APOBEC deaminase activity.

Example 4

Analysis of Somatic Mutations Attributable to AID or APOBEC3G in PIK3CA and TET2

The frequency and codon context of somatic mutations at AID, APOBEC3G and WA motifs in observed in PIK3CA from breast cancer tissue samples and TET2 from haematopoietic and lymphoid tissue samples was analysed using aggregate sample data for different patient cohorts sourced from the COSMIC database. As shown in FIGS. 12 and 13, the frequency and codon context of somatic mutations at AID, APOBEC3G and WA motifs indicated that AID and APOBEC3G were active in these tissues, and the likely cause of a significant number of observed somatic mutations.

Example 5

Analysis of Whole Exomes from Samples from Subjects with Adenoid Cystic Carcinoma The diagnostic criteria described above was used to assess the likelihood that AID and/or APOBEC3G were involved in targeted somatic mutagenesis in cells from adenoid cystic carcinoma (ACC) tissue of patients. Sequence data was obtained from a study in which whole exome sequencing was performed on 23 pretreatment primary ACC specimens and 1 local-regional lymph node metastasis, as well as corresponding matching normal salivary gland parenchymal samples (Stephens et al. (2013) J Clin Invest. 123(7):2965-2968). The exome sequencing identified 312 mutations, with a mean of 13 mutations per exome, which is relatively few compared to other solid tumors. The somatic mutations were analysed as described above to determine the frequency and codon location of mutations at <u>G</u>YW/WR<u>C</u> sites (AID), C<u>G</u>/<u>C</u>G sites (APOBEC3G) and W<u>A</u> sites.

FIG. 14 shows representative analyses of the mutations found in two patient samples: PD3185a and PD3181a. Applying the diagnostic criteria, it was observed that targeted somatic mutation occurred in nucleic acid from the PD3185a sample, and that both AID and APOBEC3G were likely to be active in cells from this sample and the cause of the targeted somatic mutagenesis. In contrast, in the sample that had the highest number of somatic mutations (PD3181a), no evidence of targeted somatic mutation was observed, with no indication that either AID or APOBEC3G were responsible for the somatic mutations present in the nucleic acid of this sample.

Overall, it was found that only 9 out of 24 of the examined ACC samples were positive for targeted somatic mutagenesis resulting from AID and/or APOBEC3G activity (Table 4). There was no correlation between the number of mutations and targeted somatic mutagenesis, or between the MYB activation score. This MYB activation score was derived to indicate whether or not a particular sample has fusions of the MYB-NFIB genes (Stephens et al. (2013) J Clin Invest. 123(7):2965-2968).

TABLE 4

| | | | TSM analysis | | |
| --- | --- | --- | --- | --- | --- |
| Sample ID | Histology | MYB activation | Mutations (n) | AID and/or APOBEC3G activity | Stat. Signif. (p value) |
| PD3178a | Cribriform | Yes | 7 | Negative | NA |
| PD3179a | Cribriform | Yes | 10 | Negative | NA |
| PD3180a | Solid | Yes | 13 | Negative | NA |
| PD3181a | Solid | Yes | 23 | Negative | NA |
| PD3182a | Cribriform | Yes | 7 | Negative | NA |
| PD3184a | Solid | Yes | 5 | Negative | NA |
| PD3185a | Solid | Yes | 11 | Positive | 0.0008 |
| PD3186a | Cribriform with solid | Yes | 13 | Positive | 0.0293 |

TABLE 4-continued

|  |  |  |  | TSM analysis | |
|---|---|---|---|---|---|
| Sample ID | Histology | MYB activation | Mutations (n) | AID and/or APOBEC3G activity | Stat. Signif. (p value) |
| PD3188a | Solid | Yes | 14 | Negative | NA |
| PD3189a | Solid | No | 8 | Negative | NA |
| PD3190a | Solid | No | 17 | Positive | 0.0039 |
| PD3191a | Solid | Yes | 11 | Negative | NA |
| PD3192a | Solid | Yes | 6 | Negative | NA |
| PD3193a | Cribriform | No | 16 | Negative | NA |
| PD3194a | Cribriform | No | 8 | Negative | NA |
| PD3195a | Solid | Yes | 10 | Positive | 0.0132 |
| PD3196a | Cribriform | Yes | 12 | Positive | 0.0032 |
| PD3197a | Cribriform | Yes | 7 | Positive | 0.0039 |
| PD3198a | Cribriform | Yes | 2 | Negative | NA |
| PD3199a | Cribriform | Yes | 8 | Positive | 0.0109 |
| PD3200a | Solid | No | 12 | Positive | 0.0019 |
| PD3208a | Solid | Yes | 7 | Positive | 0.000045 |
| PD3216a | Solid | Yes | 3 | Negative | NA |
| PD3226a | Solid | Yes | 7 | Negative | NA |

Example 6

Analysis of Whole Exomes from Samples from Subjects with Prostate Carcinoma

Exome-wide mutations data from four prostate carcinoma samples was obtained from the COSMIC database (Wellcome Trust Sanger Institute; http://cancer.sanger.ac.uk/cancergenome/projects/cosmic/) and analysed as described above to determine whether the nucleic acid in the samples contained targeted somatic mutations resulting from AID and/or APOBEC3G activity. Two of the samples were from autopsied patients with metastatic castration-resistant prostate cancer (CRPC), and the other two samples were from patients with pT2c and pT3a stage prostate cancer, respectively.

As summarised in Table 5, three of the samples were found to be positive for targeted somatic mutation resulting from AID and/or APOBEC3G activity. Interestingly, targeted somatic mutation was observed in subjects with low PSA samples, indicating that this type of analysis could be used for the early detection of prostate carcinoma before PSA levels start to rise.

FIG. 15 shows the individual analyses of the mutations found in the four patient samples. In addition to indications of AID and/or APOBEC3G activity, high numbers of G>T mutations at MC-1 sites and C>T mutations at MC-3 sites in the PR-09-3421 sample, and high numbers of G>A mutations and C>T mutations in the PR-2762 sample suggest that other APOBEC deaminases may be active in these patients.

TABLE 5

|  |  | TSM analysis | | |
|---|---|---|---|---|
| Sample ID | Stage of cancer | Mutations (n) | AID and/or APOBEC3G activity | Stat. Signif. (p value) |
| WA7 | Autopsy, CRPC | 41 | positive | 0.000127 |
| WA26 | Autopsy, CRPC | 115 | positive | 0.010397 |
| PR-09-3421 | pT3a serum PSA stage (ng/mL) - 4.8 | 49 | positive | 5.1E-05 |

TABLE 5-continued

|  |  | TSM analysis | | |
|---|---|---|---|---|
| Sample ID | Stage of cancer | Mutations (n) | AID and/or APOBEC3G activity | Stat. Signif. (p value) |
| PR-2762 | pT3a serum PSA stage (ng/mL) - 5.5 | 42 | negative | NA |

Example 7

Identification of an Aflatoxin Motif

A G>T transversion at the third position of codon 249 in TP53 is linked to aflatoxin, an exogenous mutagenic agent from Aspergillus sp., and has been used as a diagnostic marker. As shown in FIG. 5, there are a very high number of G>T mutations at the MC-3 sites in combination with G G motifs in TP53 genes from hepatocellular carcinoma (HCC) samples. To investigate this further, a whole-exome sample (HCC53T) from the COSMIC database was analysed for G>T mutations. It was observed that there were 9 G>T mutations at an MC-3 site in the whole exome, each co-incident with a GG motif. This suggests that aflatoxin causes G>T mutations at an MC-3 site off a GG motif.

Example 8

Development of Diagnostic Rules to Predict the Activity of APOBEC3H

APOBEC3H is thought to target a GA motif. To further analyse the codon context of mutations at this motif, the whole exome from tissue from a subject with bladder carcinoma was (sequence obtained from the COSMIC database) was analysed. As shown in FIG. 16, there was a predominance of G>A mutations at MC-1 sites, indicating that APOBEC3H preferentially targets mutations to the G in GA motifs when the G is at an MC-3 site, resulting in G>A mutations.

Example 9

Development of Diagnostic Rules to Predict the Activity of APOBEC3H

APOBEC3G has been suggested as targeting a CC motif in addition the CG/CG motif. To further analyse the codon context of mutations at the CC motif, the whole exomes from tissue from 8 subjects with bladder carcinoma prior to treatment (sequences obtained from the COSMIC database) were analysed. The sequences of the whole exomes from 8 subjects (B2, B5, B8-10, B13, B15 and B20) were analysed as pooled data (FIG. 17A) and the sequence of the whole exome from one subject (B13) was analysed independently (FIG. 17A). As shown in FIGS. 17A and B, there was a statistically significant predominance of C>T mutations at MC-1 sites, indicating that APOBEC3G preferentially targets mutations to the C in CC motifs when the targeted C is at a MC-1 site, resulting in C>T mutations.

The disclosure of every patent, patent application, and publication cited herein is hereby incorporated herein by reference in its entirety.

The citation of any reference herein should not be construed as an admission that such reference is available as "Prior Art" to the instant application.

Throughout the specification the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the appended claims.

What is claimed is:

1. A method for treating a cancer in a human subject, the method comprising:
    selecting a human subject on the basis of the occurrence of targeted somatic mutagenesis, wherein the occurrence of targeted somatic mutagenesis indicates that the subject is likely to have or to develop cancer; and
    exposing the subject to a therapy for treating the cancer, wherein
        targeted somatic mutagenesis has occurred when there is a higher than expected percentage or number of mutations of a mutation type at one of three positions in a codon in a plurality of mutated codons in a nucleic acid molecule in a biological sample taken from the subject, wherein:
            the nucleic acid molecule comprises the whole exome;
            the mutations are at a motif recognized or targeted by APOBEC3G;
            the number or percentage of observed G>A mutations in CG motifs at MC-2 sites in the non-transcribed strand of the nucleic acid molecule is higher than expected, or the number or percentage of observed C>T mutations in CG motifs at MC-1 sites in the non-transcribed strand of the nucleic acid molecule is higher than expected;
            the cancer is selected from the group consisting of breast, prostate, liver, colon, pancreatic, skin, cervical, lymphoid, hematopoietic and ovarian cancer; and the biological sample comprises, respectively, breast, prostate, liver, colon, pancreatic, skin, cervical, lymphoid, hematopoietic or ovarian tissue or cells; and
            the therapy comprises radiotherapy, surgery, chemotherapy, hormone ablation therapy, pro-apoptosis therapy and/or immunotherapy,
    thereby treating the cancer.

2. The method of claim 1, wherein the liver cancer is hepatocellular carcinoma, or wherein the skin cancer is melanoma.

3. The method of claim 1, wherein prior to selecting the subject, the method further comprises analyzing a sequence of the nucleic acid molecule in a biological sample taken from the subject to determine for a plurality of mutations of a mutation type at one or more motifs recognized or targeted by a mutagenic agent the codon context of those mutations to thereby identify the location of a mutation and mutation type for each of a plurality of mutated codons in the nucleic acid molecule, wherein the codon context of an individual mutation is determined by determining at which of the three positions of a corresponding mutated codon the individual mutation occurs, and determining that targeted somatic mutagenesis is likely to have occurred when there is a higher than expected percentage or number of mutations of a mutation type at one of the three positions in the plurality of mutated codons, and determining that the subject is likely to have or to develop cancer when targeted somatic mutagenesis has occurred.

4. The method of claim 3, wherein prior to analyzing the sequence of the nucleic acid molecule in a biological sample, the method further comprises sequencing the nucleic acid molecule.

5. A method for treating a cancer in a human subject, the method comprising:
    isolating a nucleic acid molecule from a biological sample obtained from a human subject;
    determining the sequence of the nucleic acid molecule;
    determining whether targeted somatic mutagenesis has occurred, wherein targeted somatic mutagenesis has occurred when there is a higher than expected percentage or number of mutations of a mutation type at one of three positions in a codon in a plurality of mutated codons in the nucleic acid molecule, wherein:
        the nucleic acid molecule comprises the whole exome;
        the mutations are at a motif recognized or targeted by APOBEC3G; and
        the number or percentage of observed G>A mutations in CG motifs at MC-2 sites in the non-transcribed strand of the nucleic acid molecule is higher than expected, or the number or percentage of observed C>T mutations in CG motifs at MC-1 sites in the non-transcribed strand of the nucleic acid molecule is higher than expected;
    selecting the subject as being likely to have cancer when targeted somatic mutagenesis has occurred; and
    exposing the subject to a therapy for treating the cancer;
        wherein the therapy comprises radiotherapy, surgery, chemotherapy, hormone ablation therapy, pro-apoptosis therapy and/or immunotherapy,
    thereby treating the cancer, wherein the cancer is selected from the group consisting of breast, prostate, liver, colon, pancreatic, skin, cervical, lymphoid, hematopoietic and ovarian cancer; and the biological sample comprises, respectively, breast, prostate, liver, colon, pancreatic, skin, cervical, lymphoid, hematopoietic or ovarian tissue or cells.

* * * * *